United States Patent [19]

Powers et al.

[11] Patent Number: 5,514,694
[45] Date of Patent: May 7, 1996

[54] PEPTIDYL KETOAMIDES

[75] Inventors: James C. Powers; Zhaozhao Li, both of Atlanta; Girish S. Patil, Marietta; Der-Lun Chu, Atlanta, all of Ga.

[73] Assignee: Georgia Tech Research Corp, Atlanta, Ga.

[21] Appl. No.: 83,009

[22] Filed: Jun. 24, 1993

Related U.S. Application Data

[63] Continuation-in-part of Ser. No. 948,454, Sep. 21, 1992, abandoned.

[51] Int. Cl.$^6$ .......................... C07K 5/062; C07K 5/065; C07K 5/068; C07K 5/072; C07K 5/075; C07K 5/078; A61K 38/05

[52] U.S. Cl. .......................... 514/357; 514/255; 514/311; 514/307; 514/471; 514/314; 514/332; 514/340; 514/252; 514/253; 514/427; 514/397; 514/399; 514/422; 514/424; 514/274; 514/263; 514/365; 514/393; 546/175; 546/140; 546/146; 546/337; 546/335; 544/336; 544/312; 544/350; 548/562; 548/338.1; 548/518; 548/550; 548/204; 548/304.1; 549/501

[58] Field of Search .................... 546/335, 175, 546/140, 337; 514/357, 255, 311, 307, 422, 424; 544/312; 548/338.1, 518, 558, 204

[56] References Cited

U.S. PATENT DOCUMENTS 4,812,442  3/1989  Boger et al. .............................. 514/18

FOREIGN PATENT DOCUMENTS 195212  9/1986  European Pat. Off. .
363284  4/1990  European Pat. Off. .

OTHER PUBLICATIONS

Hu, Arch, Biochem, Biophys., 281, pp. 271–274 (1990).
Burkhart, Tetrahedron Lett., 29, pp. 3433–3436 (1988).
Angelastro, J. Med. Chem, 33, pp. 11–13 (1990).

*Primary Examiner*—Joseph K. McKane
*Assistant Examiner*—Laura R. Cross
*Attorney, Agent, or Firm*—Deveau, Colton & Marquis

[57] ABSTRACT

A novel class of peptide α-ketoamides useful for selectively inhibiting serine proteases, selectively inhibiting cysteine proteases, generally inhibiting all serine proteases, and generally inhibiting all cysteine proteases, having the formula Y—CO—AA$^2$—AA$^1$—CO—NH—X. Processes for the synthesis of peptidyl α-ketoamide derivatives.

14 Claims, No Drawings

PEPTIDYL KETOAMIDES

This is a continuation-in-part of application Ser. No. 07/948,454 filed on Sep. 21, 1992 now abandoned.

BACKGROUND OF THE INVENTION

FIELD OF THE INVENTION

This invention relates to a novel class of peptidyl α-ketoamides useful for selectively inhibiting serine proteases, selectively inhibiting cysteine proteases, generally inhibiting all serine proteases, and generally inhibiting all cysteine proteases. Serine proteases and cysteine proteases are involved in numerous disease states and inhibitors for these enzymes can be used therapeutically for the treatment of diseases involving serine proteases or cysteine proteases. We have discovered that peptidyl α-ketoamides can be constructed to inhibit selectively individual serine or cysteine proteases or groups of serine or cysteine proteases. We have found that peptidyl ketoamides which contain hydrophobic aromatic amino acid residues in the $P_1$ site are potent inhibitors of chymases and chymotrypsin-like enzymes. Ketoamides containing small hydrophobic amino acid residues at the $P_1$ position are good inhibitors of elastases. Inhibitors of elastases and chymases are useful as anti-inflammatory agents. We have found that peptide ketoamides which contain cationic amino acid residues such as Arg and Lys in the $P_1$ site are potent inhibitors of trypsin and blood coagulation enzymes. These inhibitors are thus useful as anticoagulants. Ketoamides with aromatic amino acid residues in the $P_1$ site would be good inhibitors for cysteine proteases such as papain, cathepsin B, and calpain I and II. Thus, they would have utility as anticancer agents. Ketoamides with either aromatic amino acid residues or small hydrophobic alkyl amino acid residues at $P_1$ are good inhibitors of calpain I and II. Ketoamides with small alkyl amino acid residues such as Leu or Val at $P_2$ are also good inhibitors of the calpains. We have found that ketoamides which have both a hydrogen bonding group such as hydroxyl or alkoxy and an aromatic group are more effective inhibitors for calpain I, calpain II, cathepsin B and human neutrophil elastase. Ketoamides which contain a heterocylic group also are more potent inhibitors for calpain I, calpain II, cathepsin B and human neutrophil elastase. The ketoamides which are calpain inhibitors would be useful as neuroprotectants and can be used as therapeutics for the treatment of neurodegeneration, stroke, restenosis, and related diseases.

Nomenclature

In discussing the interactions of peptides with serine and cysteine proteases, we have utilized the nomenclature of Schechter and Berger [*Biochem. Biophys. Res. Commun.* 27, 157–162 (1967); incorporated herein by reference]. The individual amino acid residues of a substrate or an inhibitor are designated $P_1$, $P_2$, etc. and the corresponding subsites of the enzyme are designated $S_1$, $S_2$, etc. The scissile bond of the substrate is $S_1$–$S_1'$. The primary substrate recognition site of serine proteases is $S_1$. The most important recognition subsites of cysteine proteases are $S_1$ and $S_2$. With both serine and cysteine proteases, there are additional recognition sites at the prime subsites such as $S_1'$ and $S_2'$.

Amino acid residues and blocking groups are designated using standard abbreviations [see J. Biol. Chem. 260, 14–42 (1985) for nomenclature rules; incorporated herein by reference]. An amino acid residue (AA) in a peptide or inhibitor structure refers to the part structure —NH—$CHR_1$—CO—, where $R_1$ is the side chain of the amino acid residue AA. A peptide α-ketoester residue would be designated —AA—CO—OR which represents the part structure —NH—$CHR_1$—CO—CO—OR. Thus, the ethyl ketoester derived from benzoyl alanine would be designated Bz-Ala-CO-OEt which represents $C_6H_5$CO—NH—CHMe-CO— CO-OEt. Likewise, peptide ketoacid residues and peptide ketoamide residues would be designated —AA—CO—OH and —AA—CO—NH—R respectively. Thus, the ethyl keto amide derived from Z-Leu-Phe-OH would be designated Z-Leu-Phe-CO—NH-Et which represents $C_6H_5CH_2$OCO—NH—CH($CH_2$CHMe$_2$)—CO—NH—CH($CH_2$Ph)—CO—CO—NH-Et.

DESCRIPTION OF THE RELATED ART

Serine Proteases

Serine proteases play critical roles in several physiological processes such as digestion, blood coagulation, complement activation, fibrinolysis, viral infection, fertilization, and reproduction. Serine proteases are not only a physiological necessity, but also a potential hazard if they are not controlled. Uncontrolled proteolysis by elastases may cause pancreatitis, emphysema, rheumatoid arthritis, bronchial inflammation and adult respiratory distress syndrome. It has been suggested that a new trypsin-like cellular enzyme (tryptase) is involved in the infection of human immunodeficiency virus type 1 [HIV-1; Hattori et al., *FEBS Letters* 248, pp. 48–52 (1989)], which is a causative agent of acquired immunodeficiency syndrome (AIDS). Plasmin is involved in tumor invasiveness, tissue remodeling, blistering, and clot dissociation. Accordingly, specific and selective inhibitors of these proteases should be potent anticoagulants, anti-inflammtory agents, anti-tumor agents and anti-viral agents useful in the treatment of protease-related diseases [Powers and Harper, *Proteinase Inhibitors*, pp. 55–152, Barrett and Salvesen, eds., Elsevier, (1986); incorporated herein by reference]. In vitro proteolysis by chymotrypsin, trypsin or the elastase family is a serious problem in the production, purification, isolation, transport or storage of peptides and proteins. Accordingly, inhibitors of serine proteases could be useful for the prevention of such undesired proteolysis.

Elastase inhibitors are anti-inflammatory agents which can be used to treat elastase-associated inflammation including rheumatoid arthritis and emphysema. Although the naturally occurring protease inhibitor, α1-protease inhibitor (α1-PI) has been used to treat patients with emphysema, this protein inhibitor is not widely used clinically due to the high dosage needed for treatment and the difficulty of producing large quantities. Therefore small molecular weight elastase inhibitors are needed for therapy. Other low molecular weight elastase inhibitors have utility for the treatment of emphysema and inflammation (see: 1-carpapenem-3-carboxylic esters as anti-inflammatory agents, U.S. Pat. No. 4,493,839; N-carboxyl-thienamycin esters and analogs thereof as anti-inflammatory agents, U.S. Pat. No. 4,495, 197; incorporated herein by reference).

Anticoagulants and antithrombotic drugs are used in a variety of thrombotic disorders. The 1990 Physician's Desk Reference lists several anticoagulant drugs (heparin, protamine sulfate and warfarin), a few antiplatelet drugs (aspirin) and several thrombolytic agents. Heparin and warfarin are commonly used clinically for prevention and treatment of venous thrombosis and pulmonary embolism. Heparin inhibits the blood coagulation activity by accelerating the binding of natural plasma protease inhibitor antithrombin III with coagulation factors, and warfarin acts as a vitamin K antagonist and inhibits the synthesis of coagulation factors. None of the anticoagulant drugs, antithrombotic drugs, fibrinolytic agents and antiplatelet drugs are highly effective in all clinical situations and many induce side reactions [Von Kaulla, *Burger's Medicinal Chemistry*, Part II, pp 1081–1132, Wolff, ed., (1979); incorporated herein by reference]. Coagulation disorders such as disseminated intravascular coagulation, bleeding complications of medical and surgical procedures and bleeding complications of systemic illness are still difficult to manage [Ingram, Brozovic and Slater, *Bleeding Disorders*, pp 1– 413, Blackwell Scientific Publications, (1982); incorporated herein by reference]. In the treatment of patients with coagulation problems, anticoagulant or antithrombotic agents of diverse mechanisms are urgently sought in order to provide better medical care. Inhibitors for the trypsin-like enzymes involved in blood coagulation are useful anticoagulants in vivo [see for example: H-D-Phe-Pro-Arg-$CH_2Cl$, Hanson and Harker, *Proc. Natl. Acad. Sci.* 85, 3184–3188 (1988); 7-Amino-4-chloro-3-(3-isothiureidopropoxy)isocoumarin (ACITIC), Oweida, Ku, Lumsden, Kam, and Powers, *Thrombos. Res.* 58, 191–197 (1990); incorporated herein by reference].

Cysteine Proteases.

Cysteine proteases such as calpain use a cysteine residue in their catalytic mechanism in contrast to serine proteases which utilize a serine residue. Cysteine proteases include papain, cathepsin B, calpains, and several viral enzymes. Neural tissues, including brain, are known to possess a large variety of proteases, including at least two calcium stimulated proteases termed calpains. Calpains are present in many tissues in addition to the brain. Calpain I is activated by micromolar concentrations of calcium while calpain II is activated by millimolar concentrations. In the brain, calpain II is the predominant form, but calpain I is found at synaptic endings and is thought to be the form involved in long term potentiation, synaptic plasticity, and cell death. Other $Ca^{2+}$ activated cysteine proteases may exist, and the term "calpain" is used to refer to all $Ca^{2+}$ activated cysteine proteases, including calpain I and calpain II. The terms "calpain I" and "calpain II" are used herein to refer to the micromolar and millimolar activated calpains, respectively, as described above. While calpains degrade a wide variety of protein substrates, cytoskeletal proteins seem to be particularly susceptible to attack. In some cases, the products of the proteolytic digestion of these proteins by calpain are distinctive and persistent over time. Since cytoskeletal proteins are major components of certain types of cells, this provides a simple method of detecting calpain activity in cells and tissues. Thus, calpain activation can be measured indirectly by assaying the proteolysis of the cytoskeletal protein spectrin, which produces a large, distinctive and biologically persistent breakdown product when attacked by calpain [Siman, Baudry, and Lynch, *Proc. Natl. Acad. Sci. USA* 81, 3572–3576 (1984); incorporated herein by reference]. Activation of calpains and/or accumulation of breakdown products of cytoskeletal elements has been observed in neural tissues of mammals exposed to a wide variety of neurodegenerative diseases and conditions. For example, these phenomena have been observed following ischemia in gerbils and rats, following stroke in humans, following administration of the toxins kainate, trimethyltin or colchicine in rats, and in human Alzheimer's disease.

Several inhibitors of calpain have been described including peptide aldehydes such as Ac-Leu-Leu-Nle-H and leupeptin (Ac-Leu-Leu-Arg-H), as well as epoxysuccinates such as E-64. These compounds are not especially useful at inhibiting calpain in neural tissue in vivo because they are poorly membrane permeant and, accordingly, are not likely to cross the blood brain barrier very well. Also, many of these inhibitors have poor specificity and will inhibit a wide variety of proteases in addition to calpain. In addition, other classes of compounds which inhibit cysteine proteases include peptide diazomethyl ketones (Rich, D. H., in *Protease Inhibitors*, Barrett A. J., and Salversen, G., Eds., Elsevier, N.Y. 1986, pp 153–178; incorporated herein by reference). Peptide diazomethyl ketones are potentially carcinogenic and are thought to be poorly membrane permeant and to have low specificity. Thus, no effective therapy has yet been developed for most neurodegenerative diseases and conditions. Millions of individuals suffer from neurodegenerative diseases and thus, there is a need for therapies effective in treating and preventing these diseases and conditions.

Cathepsin B is involved in muscular dystrophy, myocardial tissue damage, tumor metastasis, and bone resorption. In addition, a number of viral processing enzymes, which are essential for viral infection, are cysteine proteases. Inhibitors of cysteine proteases would thus have multiple therapeutic uses.

Ketoesters.

A few amino acid and peptide ketoesters and ketoacids have been previously reported. Cornforth and Cornforth [*J. Chem. Soc.*, 93–96 (1953); incorporated herein by reference] report the synthesis of the ketoacids $PhCH_2CO$-Gly-CO—OH and Ac-Gly-CO—OH upon hydrolysis of heterocyclic molecules. Charles et al. [*J. Chem. Soc. Perkin I*, 1139–1146 (1980); incorporated herein by reference] use ketoesters for the synthesis of bicyclic heterocycles. They report the synthesis of n-Bu-CO-Ala-CO-OEt, Pr-CO-Ala-CO-OEt, cyclopentyl-CO-Ala-CO-OEt, Pr-CO-Phg-CO-OEt, and Bz-Ala-CO-OEt. Hori et al. [Peptides: *Structure and Function—Proceedings of the Ninth American Peptide Symposium* (Deber, Hruby, and Kopple, Eds.) Pierce Chemical Co., pp 819–822 (1985); incorporated herein by reference] report Bz-Ala-CO-OEt, Bz-Ala-CO—OH, Z-Ala-Ala-Abu-CO-OEt, Ala-Ala-Abu-CO-OBzl, and Z-Ala-Ala-Ala-Ala-CO-OEt (Abu=2-aminobutanoic acid or α-aminobutyric acid) and report that these compounds inhibit elastase. Trainer [*Trends Pharm. Sci.* 8, 303–307 (1987); incorporated herein by reference] comments on one of this compounds. Burkhart, J., Peet, N. P., and Bey, P. [*Tetrahedron Lett.* 29, 3433–3436 (1988); incorporated herein by reference] report the synthesis of Z-Val-Phe-CO—OMe and Bz-Phe-CO—OMe.

Mehdi et al. [*Biochem. Biophys. Res. Comm.* 166, 595–600 (1990); incorporated herein by reference] report the inhibition of human neutrophil elastase and cathepsin G by peptide α-ketoesters. Angelastro et al., [*J. Med. Chem.* 33, 13–16 (1990); incorporated herein by reference] report some α-ketoesters which are inhibitors of calpain and chymotrypsin. Hu and Abeles [*Arch. Biochem. Biophys.* 281, 271–274 (1990); incorporated herein by reference] report some peptidyl α-ketoamides and α-ketoacids which are inhibitors of cathepsin B and papain. Peet et al. [*J. Med. Chem.* 33,394–407 (1990); incorporated herein by reference] report some peptidyl α-ketoesters which are inhibitors of porcine pancreatic elastase, human neutrophil elastase, and rat & human neutrophil cathepsin G.

Ketoamides.

A single peptide ketoamide is reported in the literature by Hu and Abeles [*Arch. Biochem. Biophys.* 281, 271–274

(1990)]. This compound Z-Phe-NHCH₂CO—CO—NH-Et or Z-Phe-Gly-CO—NH-Et is reported to be an inhibitor of papain ($K_i$=1.5 mM) and cathepsin B ($K_i$=4 mM).

SUMMARY OF THE INVENTION

We have discovered that peptidyl α-ketoamide derivatives are a novel group of inhibitors for serine proteases and cysteine proteases. Inhibitors are compounds that reduce or eliminate the catalytic activity of the enzyme. We have discovered that peptidyl α-ketoamide derivatives, which have an amino acid sequence similar to that of good substrates for a particular protease, are good inhibitors for that protease. Thus, we are able to predict the structure of new inhibitors for other serine and cysteine proteases based on knowledge of their substrate specificities.

The peptidyl α-ketoamide derivatives are novel and potent inhibitors of cysteine proteases including calpains, cathepsin B, and papain. The calpain inhibitors are useful for treatment of various neurodegenerative diseases and conditions, including ischemia, stroke, and Alzheimer's disease. They will also be useful for the treatment of restenosis.

We have discovered some peptidyl α-ketoamide derivatives which are specific inhibitors for trypsin, elastase, chymotrypsin, granzymes, and other serine proteases, and some of the derivatives which are general inhibitors for groups of serine proteases. Trypsin and trypsin-like enzymes normally cleave peptide bonds in proteins and peptides where the amino acid residue on the carbonyl side of the split bond ($P_1$ residue) is Lys or Arg. Peptide α-ketoamide derivatives which have Lys or Arg at $P_1$ are thus good inhibitors for these enzymes. Elastase and elastase-like enzymes cleave peptide bonds where the $P_1$ amino acid is Ala, Val, Ser, Leu and other similar amino acids. Inhibitors with these residues at $P_1$ are good elastase inhibitors. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. Inhibitors with these residues at $P_1$ are good chymotrypsin and chymase inhibitors. All of the above enzymes have extensive secondary specificity and recognize amino acid residues removed from the $P_1$ residue.

The new protease inhibitors, especially the elastase inhibitors, trypsin inhibitors, and chymase inhibitors are useful for controlling tissue damage and various inflammatory conditions mediated by proteases such as blistering. The inhibitors for blood coagulation enzymes are useful anticoagulants and could be used to treat thrombosis.

The peptidyl α-ketoamide derivatives are also useful in vitro for inhibiting trypsin, elastase, chymotrypsin and other serine proteases of similar specificity, and for inhibiting serine proteases in general. The inhibitors can be used to identify new proteolytic enzymes encountered in research. They can also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons. For some uses a specific inhibitor would be desirable, while in other cases, an inhibitor with general specificity would be preferred.

We have also discovered several new processes for the synthesis of α-ketoamide derivatives of peptides from easily available peptide derivatives. These processes should be widely applicable to the synthesis of many new α-ketoamide derivatives of peptides.

DETAILED DESCRIPTION OF THE INVENTION

Peptide α-ketoamides are transition state analog inhibitors for serine proteases and cysteine proteases. Peptide α-ketoamides containing hydrophobic amino acid residues in the $P_1$ site have been found to be excellent inhibitors of serine proteases including porcine pancreatic elastase and bovine chymotrypsin. We show that peptide α-ketoamides containing amino acid residues with cationic side chains in the $P_1$ site will be excellent inhibitors of several serine proteases including bovine trypsin, bovine thrombin, human plasma kallikrein, porcine pancreatic kallikrein, human factor XIa and human plasmin. Peptide α-ketoamides containing amino acid residues with hydrophobic side chain at the $P_1$ site have also been found to be excellent inhibitors of several cysteine proteases including papain, cathepsin B, calpain I, and calpain II. Inhibitors with a $P_2$ Leu, Val or similar residues are particularly good inhibitors for the calpains. Addition of a heterocyclic, aromatic, or hydrogen bonding group to the amide portion of the inhibitor results in improved inhibitory potency and specificity due to interaction with S' subsites of the targeted enzyme.

These structures may be used in vivo to treat diseases such as emphysema, adult respiratory distress syndrome, rheumatoid arthritis and pancreatitis which result from uncontrolled proteolysis by elastase, chymotrypsin, trypsin and related serine proteases. These inhibitors may be used in vitro to prevent proteolysis which occurs in the process of production, isolation, purification, storage or transport of peptides and proteins. These inhibitors may be useful as therapeutic agents for treatment of neurodegeneration, viral infections, muscular dystrophy, myocardial tissue damage, tumor metastasis, restenosis, and bone resorption.

Detailed Description of Peptide α-Ketoamides

The novel class of dipeptide α-ketoamides have the following structural formula:

or a pharmaceutically acceptable salt, wherein

Y is selected from the group consisting of $C_{1-4}$ alkyl monosubstituted with phenyl, $C_{1-4}$ alkyl disubstituted with phenyl, $C_{1-4}$ alkyl monosubstituted with 1-naphthyl, $C_{1-4}$ alkyl monosubstituted with 2-naphthyl, $C_{1-4}$ alkoxy monosubstituted with phenyl, $C_{1-4}$ alkoxy disubstituted with phenyl, ArCH₂O—, ArO—, ArCH₂NH—, ArNH—, $M^1$—(CH₂)$_q$—, and $M^2$—(CH₂)$_q$—O;

wherein Ar is selected from the group consisting of phenyl, phenyl monosubstituted with J, phenyl disubstituted with J, 1-naphthyl, 1-naphthyl monosubstituted with J, 2-naphthyl, and 2-naphthyl monosubstituted with J;

J is selected from the group consisting of halogen, OH, CN, NO₂, NH₂, COOH, CO₂Me, CO₂Et, CF₃, $C_{1-4}$ alkoxy, $C_{1-4}$alkylamine, $C_{2-8}$ dialkylamine, $C_{1-4}$ perfluoroalkyl, and —N(CH₂CH₂)₂O;

$M^1$ is selected from the group consisting of 2-furyl, 2-tetrahydrofuryl, 2-pyridyl, 3-pyridyl, 4-pyridyl, 2-pyrazinyl, 2-quinolinyl, 1-tetrahydroquinolinyl, 1-isoquinolinyl, 2-tetrahydroisoquinolinyl, and —N(CH$_2$CH$_2$)$_2$O;

q=0-2;

M$^2$ is selected from the group consisting of 2-furyl, 2-tetrahydrofuryl, 2-pyridyl, 2-pyrazinyl, 2-quinolinyl, 2-tetrahydroquinolinyl, 1-isoquinolinyl, and 1-tetrahydroisoquinolinyl;

AA$^2$ is an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, NH$_2$—CH(CH$_2$—CHEt$_2$)—COOH, alpha-aminoheptanoic acid, NH$_2$—CH(CH$_2$-cyclohexyl)—COOH, NH$_2$—CH(CH$_2$-cyclopentyl)—COOH, NH$_2$—CH(CH$_2$-cyclobutyl)—COOH, NH$_2$—CH(CH$_2$-cyclopropyl)—COOH, 5,5,5-trifluoroleucine, and hexafluoroleucine;

AA$^1$ is an amino acid with the L configuration, D configuration, or DL configuration at the α-carbon selected from the group consisting of alanine, 4-chlorophenylalanine valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, NH$_2$CH(CH$_2$-CHEt$_2$)—COOH, alpha-aminoheptanoic acid, NH$_2$—CH(CH$_2$-1-napthyl)—COOH, NH$_2$—CH(CH$_2$-2-napthyl)—COOH, NH$_2$—CH(CH$_2$-cyclohexyl)—COOH, NH$_2$—CH(CH$_2$-cyclopentyl)—COOH, NH$_2$—CH(CH$_2$-cyclobutyl)—COOH, NH$_2$—CH(CH$_2$-cyclopropyl)—COOH, 5,5,5-trifluoroleucine, and hexafluoroleucine;

X is selected from the group consisting of
a) —CH$_2$CH(OH)—R$^1$ and
b) —(CH$_2$)$_n$—R$^3$;

R$_1$ is selected from the group consisting of phenyl, phenyl monosubstituted with J, phenyl disubstituted with J, phenyl trisubstituted with J, pentafluorophenyl,

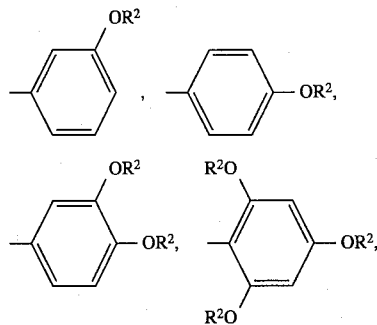

1-naphthyl, 1-naphthyl monosubstituted with J, 1-naphthyl disubstituted with J, 2-naphthyl, 2-naphthyl monosubstituted with J, 2-naphthyl disubstituted with J, 2-pyridyl, 2-quinolinyl, and 1-isoquinolinyl;

R$^2$ represents C$_{1-4}$ alkyl, C$_{1-4}$ alkyl substituted with phenyl, phenyl and phenyl substituted with J;

n=1-3;

R$^3$ is selected from the group consisting of 2-furyl, 2-furyl monosubstituted with J, 2-pyridyl, 2-pyridyl monosubstituted with J, 3-pyridyl, 3-pyridyl monosubstituted with J, 4-pyridyl, 4-pyridyl monosubstituted with J, 2-quinolinyl, 2-quinolinyl monosubstituted with J, 1-isoquinolinyl, 1-isoquinolinyl monosubstituted with J,

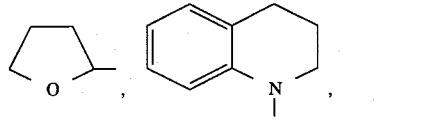

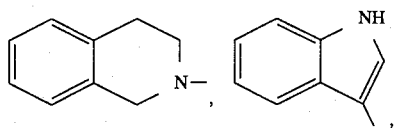

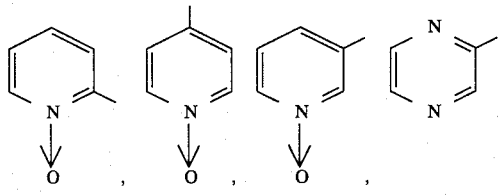

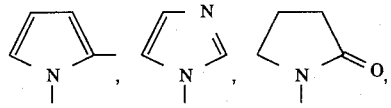

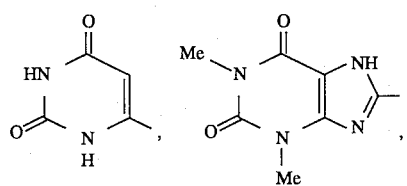

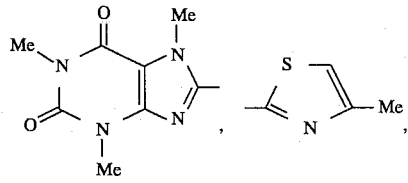

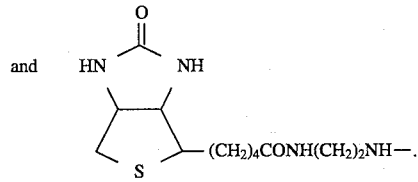

and 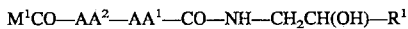

The novel class of dipeptide α-ketoamides also have the following structural formula:

M$^1$CO—AA$^2$—AA$^1$—CO—NH—CH$_2$CH(OH)—R$^1$ or a pharmaceutically acceptable salt, wherein M$^1$ is selected from the group consisting of C$_{1-4}$ alkyl monosubstituted with phenyl, C$_{1-4}$ alkyl disubstituted with phenyl, C$_{1-4}$ alkyl monosubstituted with 1-naphthyl, C$_{1-4}$ alkyl monosubstituted with 2-naphthyl, C$_{1-4}$ alkoxy monosubstituted with phenyl, C$_{1-4}$ alkoxy disubstituted with phenyl, ArCH$_2$O—, ArO—, ArCH$_2$NH—, and ArNH—;

wherein Ar is selected from the group consisting of phenyl, phenyl monosubstituted with J, phenyl disubstituted with J, 1-naphthyl, 1-naphthyl monosubstituted with J, 2-naphthyl, and 2-naphthyl monosubstituted with J;

J is selected from the group consisting of halogen, OH, CN, $NO_2$, $NH_2$, COOH, $CO_2Me$, $CO_2Et$, $CF_3$, $C_{1-4}$ alkoxy, $C_{1-4}$ alkylamine, $C_{2-8}$ dialkylamine, $C_{1-4}$ perfluoroalkyl, and $—N(CH_2CH_2)_2O$;

$AA^2$ is an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, $NH_2$—$CH(CH_2$—$CHEt_2)$—COOH, alpha-aminoheptanoic acid, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl)—COOH, 5,5,5-trifluoroleucine, and hexafluoroleucine;

$AA^1$ is an amino acid with the L configuration, D configuration, or DL configuration at the α-carbon selected front the group consisting of alanine, valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-1-napthyl)—COOH, $NH_2$—$CH(CH_2$-2napthyl)—COOH, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl)—COOH, 5,5,5-trifluoroleucine, and hexafluoroleucine;

$R^1$ is selected from the group consisting of phenyl, phenyl monosubstituted with J, phenyl disubstituted with J, phenyl trisubstituted with J, pentafluorophenyl,

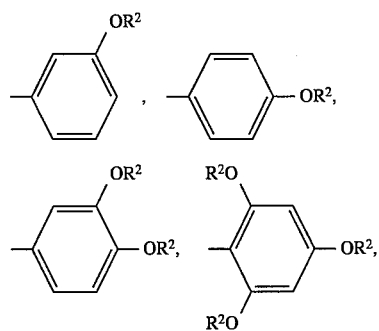

1-naphthyl, 1-naphthyl monosubstituted with J, 1-naphthyl disubstituted with J, 2-naphthyl, 2-naphthyl monosubstituted with J, 2-naphthyl disubstituted with J, 2-pyridyl, 2-quinolinyl, and 1-isoquinolinyl;

$R^2$ represents $C_{1-4}$ alkyl substituted with phenyl, phenyl and phenyl substituted with J.

The novel class of dipeptide α-ketoamides also have the following structural formula:

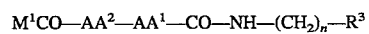

or a pharmaceutically acceptable salt, wherein $M^1$ is selected from the group consisting of $C_{1-4}$ alkyl monosubstituted with phenyl, $C_{1-4}$ alkyl disubstituted with phenyl, $C_{1-4}$ alkyl monosubstituted with 1-naphthyl, $C_{1-4}$ alkyl monosubstituted with 2-naphthyl, $C_{1-4}$ alkoxy monosubstituted with phenyl, $C_{1-4}$ alkoxy disubstituted with phenyl, $ArCH_2O$—, ArO—, $ArCH_2NH$—, and ArNH—;

wherein Ar is selected from the group consisting of phenyl, phenyl monosubstituted with J, phenyl disubstituted with J, 1-naphthyl, 1-naphthyl monosubstituted with J, 2-naphthyl, and 2-naphthyl monosubstituted with J;

J is selected from the group consisting of halogen, OH, CN, $NO_2$, $NH_2$, COOH, $CO_2Me$, $CO_2Et$, $CF_3$, $C_{1-4}$ alkoxy, $C_{1-4}$ alkylamine, $C_{2-8}$ dialkylamine, $C_{1-4}$ perfluoroalkyl, and $—N(CH_2CH_2)_2O$;

$AA^2$ is an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl)—COOH, 5,5,5-trifluoroleucine, and hexafluoroleucine;

$AA^1$ is an amino acid with the L configuration, D configuration, or DL configuration at the α-carbon selected from the group consisting of alanine, valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-1-napthyl)—COOH, $NH_2$—$CH(CH_2$-2-napthyl)—COOH, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl)—COOH, 5,5,5-trifluoroleucine, and hexafluoroleucine;

n=1–3;

$R^3$ is selected from the group consisting of 2-furyl, 2-furyl monosubstituted with J, 2-pyridyl, 2-pyridyl monosubstituted with J, 3-pyridyl, 3-pyridyl monosubstituted with J, 4-pyridyl, 4-pyridyl monosubstituted with J, 2-quinolinyl, 2-quinolinyl monosubstituted with J, 1-isoquinolinyl, 1-isoquinolinyl monosubstituted with J,

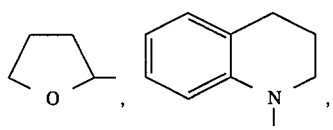

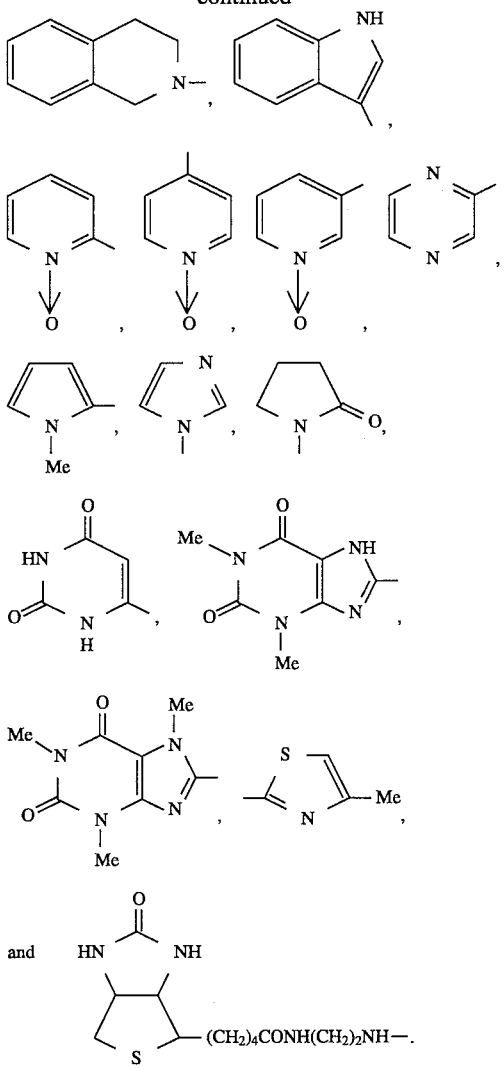

and 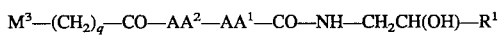

The novel class of dipeptide α-ketoamides also have the following structural formula:

$$M^3—(CH_2)_q—CO—AA^2—AA^1—CO—NH—CH_2CH(OH)—R^1$$

or a pharmaceutically acceptable salt, wherein $M^3$ is selected from the group consisting of 2-furyl, 2-tetrahydrofuryl, 2-pyridyl, 3-pyridyl, 4-pyridyl, 2-pyrazinyl, 2-quinolinyl, 1-tetrahydroquinolinyl, 1-isoquinolinyl, 2tetrahydroquinolinyl, and —N(CH$_2$CH$_2$)$_2$O;

q=0–2;

$AA^2$ is an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-cyclohexyl)—COOH, NH$_2$—CH(CH$_2$-cyclopentyl)—COOH, NH$_2$—CH(CH$_2$-cyclobutyl)—COOH, NH$_2$—CH(CH$_2$-cyclopropyl)—COOH, 5,5,5-trifluoroleucine, and hexafluoroleucine;

$AA^1$ is an amino acid with the L configuration, D configuration, or DL configuration at the α-carbon selected from the group consisting of alanine, valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-1-napthyl)—COOH, NH$_2$—CH(CH$_2$-2-napthyl)—COOH, NH$_2$—CH(CH$_2$-cyclohexyl)—COOH, NH$_2$—CH(CH$_2$-cyclopentyl)—COOH, NH$_2$—CH(CH$_2$-cyclobutyl)—COOH, NH$_2$—CH(CH$_2$-cyclopropyl)—COOH, 5,5,5-rifluoroleucine, and hexafluoroleucine;

$R_1$ is selected from the group consisting of phenyl, phenyl monosubstituted with J, phenyl disubstituted with J, phenyl trisubstituted with J, pentafluorophenyl,

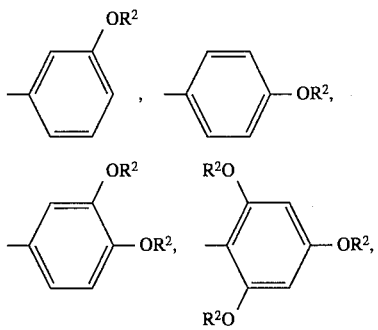

1-naphthyl, 1-naphthyl monosubstituted with J, 1-naphthyl disubstituted with J, 2-naphthyl 2-naphthyl monosubstituted with J, 2-naphthyl disubstituted with J, 2-pyridyl, 2-quinolinyl, and 1-isoquinolinyl;

$R^2$ represents $C_{1-4}$ alkyl substituted with phenyl, phenyl and phenyl substituted with J.

J is selected from the group consisting of halogen, OH, CN, NO$_2$, NH$_2$, COOH, CO$_2$Me, CO$_2$Et, CF$_3$, $C_{1-4}$ alkoxy, $C_{1-4}$ alkylamine, $C_{2-8}$ dialkylamine, $C_{1-4}$ perfluoroalkyl, and N(CH$_2$CH$_2$)$_2$O;

The novel class of dipeptide α-ketoamides also have the following structural formula:

or a pharmaceutically acceptable salt, wherein $M^3$ is selected from the group consisting of 2-furyl, 2-tetrahydrofuryl, 2-pyridyl, 3-pyridyl, 4-pyridyl, 2-pyrazinyl, 2-quinolinyl, 1-tetrahydroquinolinyl, 1-isoquinolinyl, 2-tetrahydroisoquinolinyl, and —N(CH$_2$CH$_2$)$_2$O;

q=0–2

$AA^2$ is an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-cyclohexyl)—COOH, NH$_2$—

CH(CH₂-cyclopentyl)—COOH, NH₂—CH(CH₂-cyclobutyl)—COOH, NH₂—CH(CH₂-cyclopropyl)—COOH, 5,5,5-trifluoroleucine, and hexafluoroleucine;

AA¹ is an amino acid with the L configuration, D configuration, or DL configuration at the a-carbon selected from the group consisting of alanine, valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, NH₂—CH(CH₂CHEt₂)—COOH, alpha-aminoheptanoic acid, NH₂—CH(CH₂-1-napthyl)—COOH, NH₂—CH(CH₂-2-napthyl)—COOH, NH₂—CH(CH₂-cyclohexyl)—COOH, NH₂ —CH(CH₂-cyclopentyl)—COOH, NH₂—CH(CH₂-cyclobutyl)—COOH, NH₂—CH(CH₂-cyclopropyl)—COOH, 5,5,5-rifluoroleucine, and hexafluoroleucine;

n=1–3;

R³ is selected from the group consisting of 2-furyl, 2-furyl monosubstituted with J, 2-pyridyl, 2-pyridyl monosubstituted with J, 3-pyridyl, 3-pyridyl monosubstituted with J, 4-pyridyl, 4-pyridyl monosubstituted with J, 2-quinolinyl, 2-quinolinyl monosubstituted with J, 1-isoquinolinyl, 1-isoquinolinyl monosubstituted with J,

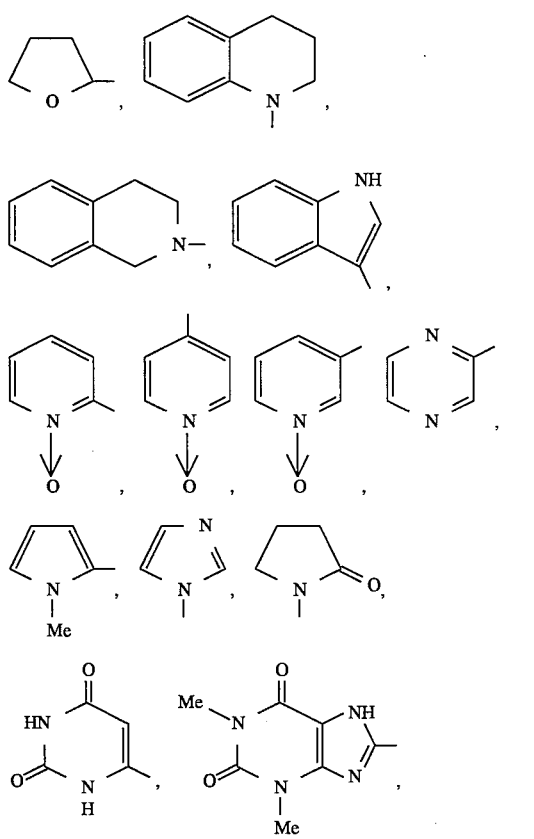

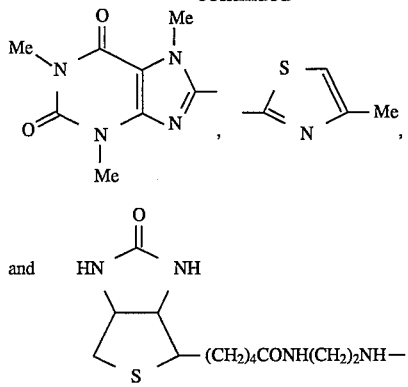

and 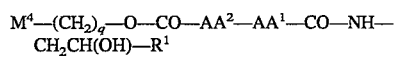

J is selected from the group consisting of halogen, OH, CN, NO₂, NH₂, COOH, CO₂Me, CO₂Et, CF₃, C₁₋₄ alkoxy, C₁₋₄ alkylamine, C₂₋₈ dialkylamine, C₁₋₄ perfluoroalkyl, and N(CH₂CH₂)₂O;

The novel class of dipeptide α-ketoamides also have the following structural formula:

M⁴—(CH₂)$_q$—O—CO—AA²—AA¹—CO—NH—CH₂CH(OH)—R¹ or a pharmaceutically acceptable salt, wherein

M⁴ is selected from the group consisting of 2-furyl, 2-tetrahydrofuryl, 2-pyridyl, 2-pyrazinyl, 2-quinolinyl, 2-tetrahydroquinolinyl, 1-isoquinolinyl, and 1-tetrahydroisoquinolinyl;

q=0–2;

AA² is an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, NH₂—CH(CH₂CHEt₂)—COOH, alpha-aminoheptanoic acid, NH₂—CH(CH₂-cyclohexyl)—COOH, NH₂—CH(CH₂-cyclopentyl)—COOH, NH₂—CH(CH₂-cyclobutyl)—COOH, NH₂—CH(CH ₂-cyclopropyl)—COOH, 5,5,5-trifluoroleucine, and hexafluoroleucine;

AA¹ is an amino acid with the L configuration, D configuration, or DL configuration at the α-carbon selected from the group consisting of alanine, valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, NH₂—CH(CH₂CHEt₂)—COOH, alpha-aminoheptanoic acid, NH₂—CH(CH₂-1-napthyl)—COOH, NH₂—CH(CH₂-2-napthyl)—COOH, NH₂—CH(CH₂-cyclohexyl)—COOH, NH₂—CH(CH₂ -cyclopentyl)—COOH, NH₂—CH(CH₂-cyclobutyl)—COOH, NH₂—CH(CH₂-cyclopropyl)—COOH, 5,5,5-rifluoroleucine, and hexafluoroleucine;

R¹ is selected from the group consisting of phenyl, phenyl monosubstituted with J, phenyl disubstituted with J, phenyl trisubstituted with J, pentafluorophenyl,

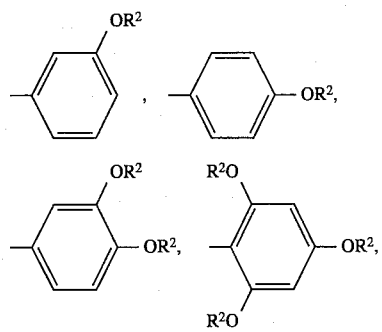

1-naphthyl, 1-naphthyl monosubstituted with J, 1-naphthyl disubstituted with J, 2-naphthyl 2-naphthyl monosubstituted with J, 2-naphthyl disubstituted with J, 2-pyridyl, 2-quinolinyl, and 1-isoquinolinyl;

$R^2$ represents $C_{1-4}$ alkyl substituted with phenyl, phenyl and phenyl substituted with J.

J is selected from the group consisting of halogen, OH, CN, $NO_2$, $NH_2$, COOH, $CO_2Me$, $CO_2Et$, $CF_3$, $C_{1-4}$ alkoxy, $C_{1-4}$ alkylamine, $C_{2-8}$ dialkylamine, $C_{1-4}$ perfluoroalkyl, and $N(CH_2CH_2)_2O$;

The novel class of dipeptide α-ketoamides also have the following structural formula:

or a pharmaceutically acceptable salt, wherein $M^4$ is selected from the group consisting of 2-furyl, 2-tetrahydrofuryl, 2-pyridyl, 2-pyrazinyl, 2-quinolinyl, 2-tetrahydroquinolinyl, 1-isoquinolinyl, and 1-tetrahydroisoquinolinyl;

q=0–2;

$AA^2$ is an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$ -cyclopropyl)—COOH, 5,5,5-trifluoroleucine, and hexafluoroleucine;

$AA^1$ is an amino acid with the L configuration, D configuration, or DL configuration at the a-carbon selected from the group consisting of alanine, valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-1-napthyl)—COOH, $NH_2$—$CH(CH_2$-2-napthyl)—COOH, $NH_2$—$CH(CH_2$-cyclohexyl)—COOH, $NH_2$—$CH(CH_2$ -cyclopentyl)—COOH, $NH_2$—$CH(CH_2$-cyclobutyl)—COOH, $NH_2$—$CH(CH_2$-cyclopropyl)—COOH, 5,5,5-trifluoroleucine, and hexafluoroleucine;

n=1–3;

$R^3$ is selected from the group consisting of 2-furyl, 2-furyl monosubstituted with J, 2-pyridyl, 2-pyridyl monosubstituted with J, 3-pyridyl, 3-pyridyl monosubstituted with J, 4-pyridyl, 4-pyridyl monosubstituted with J, 2-quinolinyl, 2-quinolinyl monosubstituted with J, 1-isoquinolinyl, 1-isoquinolinyl monosubstituted with J,

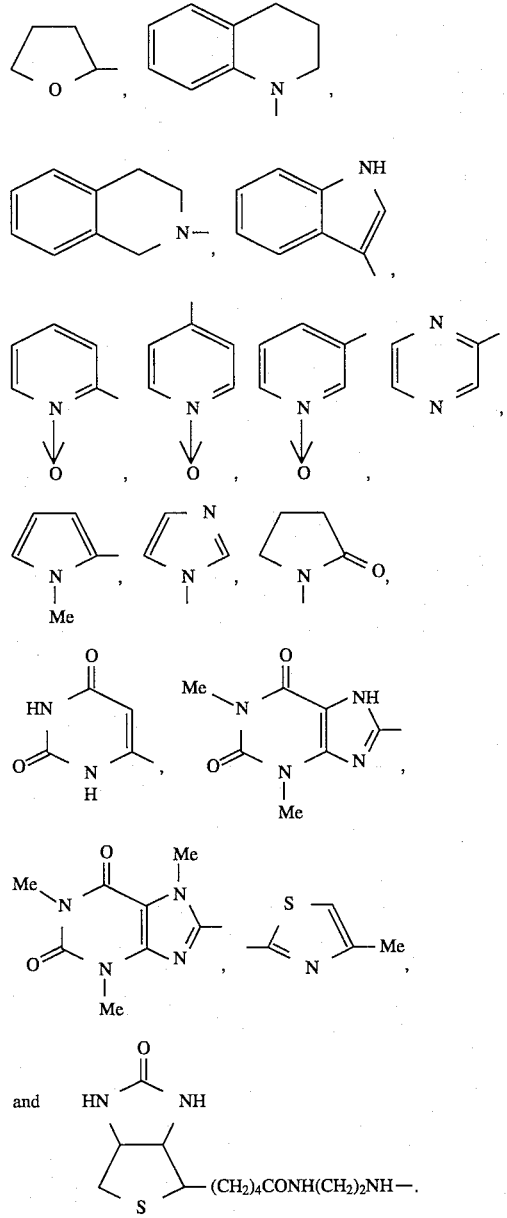

and 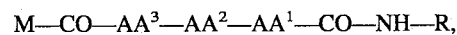

J is selected from the group consisting of halogen, OH, CN, $NO_2$, $NH_2$, COOH, $CO_2Me$, $CO_2Et$, $CF_3$, $C_{1-4}$ alkoxy, $C_{1-4}$ alkylamine, $C_{2-8}$ dialkylamine, $C_{1-4}$ perfluoroalkyl, and $N(CH_2CH_2)_2O$.

Processes For the Synthesis of α-Ketoamides

We have also discovered a process for the synthesis of α-ketoamides with the structures M—CO—$AA^2$—$AA^1$—CO—NH—R and
M—CO—$AA^3$—$AA^2$—$AA^1$—CO—NH—R,
wherein M is selected from the group consisting of $C_{1-4}$ alkyl monosubstituted with phenyl, $C_{1-4}$ alkyl disubstituted with phenyl, $C_{1-4}$ alkyl monosubstituted with 1-naphthyl, $C_{1-4}$ alkyl monosubstituted with 2-naphthyl, $C_{1-4}$ alkoxy monosubstituted with phenyl, $C_{1-4}$ alkoxy disubstituted with phenyl, $Ar^1CH_2O$—, $Ar^1O$—, $Ar^1CH_2NH$—, $Ar^1NH$— and Heterocycle$^1(CH_2)_q$—;

$Ar^1$ is selected from the group consisting of phenyl, phenyl monosubstituted with J, phenyl disubstituted with J, 1-naphthyl, 1-naphthyl monosubstituted with J, 2-naphthyl, and 2-naphthyl monosubstituted with J;

J is selected from the group consisting of halogen, OH, CN, $NO_2$, $NH_2$, COOH, $CO_2Me$, $CO_2Et$, $CF_3$, $C_{1-4}$ alkoxy, $C_{1-4}$ alkylamine, $C_{2-8}$ dialkylamine, $C_{1-4}$ perfluoroalkyl, and —$N(CH_2CH_2)_2O$;

Heterocycle$^1$ is selected from the group consisting of 2-furyl, 2-tetrahydrofuryl, 2-pyrazinyl, 3-pyridyl, 4-pyridyl, 2-quinolinyl, 1-tetrahydroquinolinyl, 1-isoquinolinyl, 2-tetrahydroisoquinolinyl, and —$N(CH_2CH_2)_2O$;

q=0–2;

$AA^1$, $AA^2$ and $AA^3$ are side chain blocked or unblocked α-amino acids with the L configuration, D configuration, or DL configuration at the α-carbon selected independently from the group consisting of alanine, valine, leucine, isoleucine, histidine, proline, methionine, methionine sulfoxide, phenylalanine, serine, threonine, phenylglycine, norleucine, norvaline, arginine, lysine, tryptophan, glycine, cysteine, tyrosine, asparagine, glutamine, aspartic acid, glutamic acid, alpha-aminobutyric acid, O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl)—COOH, $NH_2$—$CH(CH_2$-1-naphthyl)—COOH, $NH_2$—$CH(CH_2$-2-naphthyl)—COOH, 5,5,5-trifluoroleucine, and hexafluoroleucine;

R is selected from the group consisting of H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group substituted with K, $C_{1-10}$ alkyl with a morpholine [—$N(CH_2CH_2)_2O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), —NH—$CH_2CH_2$-(3-indolyl), $CH_2CH(OH)$-$Ar^2$ and $(CH_2)_n$-Heterocycle$^2$;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy—CO—, and $C_{1-10}$ alkyl-S—;

$Ar^2$ is selected from the group consisting of phenyl, phenyl monosubstituted with J, phenyl disubstituted with J, phenyl trisubstituted with J, pentafluorophenyl, $C_6H_4$(3-$OR^2$), $C_6H_4$(4-$OR^2$), $C_6H_3$(3,4-$(OR^2)_2$), $C_6H_2$(2,4,6 -$(OR^2)_3$), 1-naphthyl monosubstituted with J, 1-naphthyl disubstituted with J, 2-naphthyl, 2-naphthyl monosubstituted with J, 2-naphthyl disubstituted with J, 2-pyridyl, 2-quinolinyl, and 1-isoquinolinyl;

$R^2$ represents $C_{1-4}$ alkyl substituted with phenyl, phenyl and phenyl substituted with J.

Heterocycle$^2$ is selected from the group consisting of 2-furyl, 2-furyl monosubstituted with J, 2-tetrahydrofuryl, 2-pyridyl, 2-pyridyl monosubstituted with J, 3-pyridyl, 3-pyridyl monosubstituted with J, 4-pyridyl, 4-pyridyl monosubstituted with J, 2-pyrazinyl, 2-quinolinyl, 2-quinolinyl monosubstituted with J, 1-isoquinolinyl, 1-isoquinolinyl monosubstituted with J, 1-tetrahydroquinolinyl, 2-tetrahydroisoquinolinyl, 3-indolyl, 2-pyridyl-N-oxide, 3-pyridyl-N-oxide, 4-pyridyl-N-oxide, 2-(N-methyl-2-pyrrolyl), 1-imidazolyl, 1-pyrrolidinyl-2-one, 2-(5-methyl-3-thiazolyl), $(CH_2)_2$—NH-biotin;

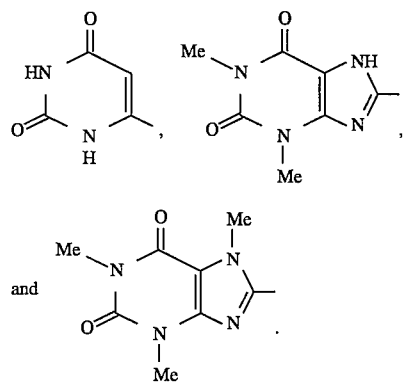

comprising the steps:

(a) Protecting the α-ketone carbonyl of a peptidyl α-ketoester with the structures M—CO—$AA^2$—$AA^1$—$COOR^6$ and
M—CO—$AA^3$—$AA^2$—$AA^1$—$COOR^6$, wherein $R^6$ is selected from the group consisting of $C_{1-6}$ alkyls and $C_{1-6}$ alkyls monosubstituted with phenyl, by treatment with a blocking reagent in the presence of a Lewis acid in an organic solvent at 0°–100° C. for 1–48 hours, wherein the preferred blocking reagent is 1,2-ethanedithiol;

the preferred Lewis acids are selected from the group consisting of $BF_3.Et_2O$, 4-toluene sulfonic acid, $AlCl_3$ and $ZnCl_2$;

the preferred organic solvents are selected from the group consisting of $CH_2Cl_2$, $CHCl_3$, $Et_2O$ and THF;

(b) Treating the product with a primary amine $RNH_2$ in an organic solvent at 0°–100° C. for 1–72 hours, wherein the preferred organic solvents are selected from the group consisting of EtOH, THF, $CH_2Cl_2$ and DMF;

(c) Removing the blocking group from the α-carbonyl to give the desired peptidyl α-ketoamide.

We have also discovered another process for the synthesis of peptidyl α-ketoamides with the structures M—CO—$AA^2$—$AA^1$—CO—NH—R and
M—CO—$AA^3$—$AA^2$—$AA^1$—CO—NH—R, wherein M is selected from the group consisting of $C_{1-4}$ alkyl monosubstituted with phenyl, $C_{1-4}$ alkyl disubstituted with phenyl, $C_{1-4}$ alkyl monosubstituted with 1-naphthyl, $C_{1-4}$ alkyl monosubstituted with 2-naphthyl, $C_{1-4}$ alkoxy monosubstituted with phenyl, $C_{1-4}$ alkoxy disubstituted with phenyl, $Ar^1CH_2O—$, $Ar^1O—$, $Ar^1CH_2NH—$, $Ar^1NH—$ and Heterocycle$^1(CH_2)_q—$;

$Ar^1$ is selected from the group consisting of phenyl, phenyl monosubstituted with J, phenyl disubstituted with J, 1-naphthyl, 1-naphthyl monosubstituted with J, 2-naphthyl, and 2-naphthyl monosubstituted with J;

J is selected from the group consisting of halogen, OH, CN, $NO_2$, $NH_2$, COOH, $CO_2Me$, $CO_2Et$, $CF_3$, $C_{1-4}$ alkoxy, $C_{1-4}$ alkylamine, $C_{2-8}$ dialkylamine, $C_{1-4}$ perfluoroalkyl, and $—N(CH_2CH_2)_2O$;

Heterocycle 1 is selected from the group consisting of 2-furyl, 2-tetrahydrofuryl, 2-pyridyl, 3-pyridyl, 4-pyridyl, 2-pyrazinyl, 2-quinolinyl, 1-tetrahydroquinolinyl, 1-isoquinolinyl, 2-tetrahydroisoquinolinyl, and $—N(CH_2CH_2)_2O$;

q=0–2;

$AA^1$, $AA^2$ and $AA^3$ are side chain blocked or unblocked α-amino acids with the L configuration, D configuration, or DL configuration at the a-carbon selected independently from the group consisting of alanine, valine, leucine, isoleucine, histidine, proline, methionine, methionine sulfoxide, phenylalanine, serine, threonine, phenylglycine, norleucine, norvaline, arginine, lysine, tryptophan, glycine, cysteine, tyrosine, asparagine, glutamine, aspartic acid, glutamic acid, alpha-aminobutyric acid, O-methylserine, O-ethylserine, S-methylcysteine, S-ethylcysteine, S-benzylcysteine, $NH_2$—CH($CH_2CHEt_2$)—COOH, alpha-aminoheptanoic acid, $NH_2$—CH($CH_2$-cyclohexyl)—COOH, $NH_2$—CH($CH_2$-cyclopentyl)—COOH, $NH_2$—CH($CH_2$-cyclobutyl)—COOH, $NH_2$—CH($CH_2$-cyclopropyl)—COOH, $NH_2$—CH($CH_2$-1-naphthyl)—COOH, $NH_2$—CH($CH_2$-2-naphthyl)—COOH, 5,5,5-trifluoroleucine, and hexafluoroleucine;

R is selected from the group consisting of H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group substituted with K, $C_{1-10}$ alkyl with a morpholine [$—N(CH_2CH_2)_2O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, $—CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, $—NH—CH_2CH_2$-(4-hydroxyphenyl), $—NH—CH_2CH_2$-(3-indolyl), $CH_2CH(OH)$—$Ar^2$ and $(CH_2)_n$—Heterocycle$^2$;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy—CO—, and $C_{1-10}$ alkyl—S—;

$Ar^2$ is selected from the group consisting of phenyl, phenyl monosubstituted with J, phenyl disubstituted with J, phenyl trisubstituted with J, pentafluorophenyl, $C_6H_4$(3-$OR^2$), $C_6H_4$(4-$OR^2$), $C_6H_3$(3,4-$(OR^2)_2$), $C_6H_2$ (2,4,6-$(OR^2)_3$, 1-napthyl, 1-napthyl monosubstituted with J, 1-naphthyl disubstituted with J, 2-naphthyl, 2-naphthyl monosubstituted with J, 2-naphthyl disubstituted with J, 2-pyridyl, 2-quinolinyl, and 1-isoquinolinyl;

$R^2$ represents $C_{1-4}$ alkyl substituted with phenyl, phenyl and phenyl substituted with J.

Heterocycle$^2$ is selected from the group consisting of 2-furyl, 2-furyl monosubstituted with J, 2-tetrahydrofuryl, 2-pyridyl, 2-pyridyl monosubstituted with J, 3-pyridyl, 3-pyridyl monosubstituted with J, 4-pyridyl, 4-pyridyl monosubstituted with J, 2-pyrazinyl, 2-quinolinyl, 2-quinolinyl monosubstituted with J, 1-isoquinolinyl, 1-isoquinolinyl monosubstituted with J, 1-tetrahydroquinolinyl, 2-tetrahydroisoquinolinyl, 3-indolyl, 2-pyridyl-N-oxide, 3-pyridyl-N-oxide, 4-pyridyl-N-oxide, 2-(N-methyl-2-pyrrolyl), 1-imidazolyl, 1-pyrrolidinyl-2-one, 2-(5-methyl-3-thiazolyl), $(CH_2)2$-NH-biotin;

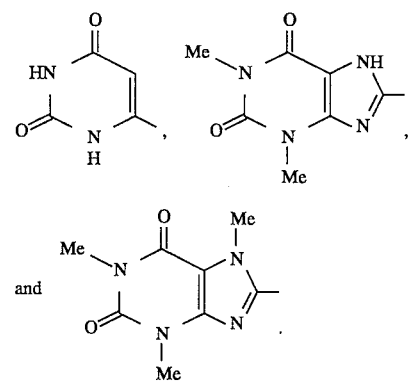

comprised of the steps:

(a) Hydrolyzing a peptidyl α-ketoester with the structures
M—CO—$AA^2$—$AA^1$—$COOR^6$ and
M—CO—$AA^3$—$AA^2$—$AA^1$—$COOR^6$,
wherein $R^6$ is selected from the group consisting of $C_{1-6}$ alkyls and $C_{1-6}$ alkyls monosubstituted with phenyl; by treating the peptidyl α-ketoester with a hydrolysis reagent in an appropriate solvent at 0°–100° C. for 1–24 hours to give the corresponding peptidyl α-ketoacid, wherein the preferred hydrolysis reagents are selected from the group consisting of NaOH, KOH, EtONa and EtOK;

the preferred solvent are selected from the group consisting of water, MeOH, EtOH, THF and DMF;

(b) Coupling the product peptidyl α-ketoacid with a primary amine $RNH_2$ in an organic solvent at 0°–100° C. for 1–72 hours to give the desired peptidyl α-ketoamide,
wherein the preferred coupling conditions are selected from the group consisting of treatment with 1, 1-carbonyldiimidazole, treatment with dicyclohexylcarbodiimide, and treatment with dicyclohexylcarbodiimide-1-hydroxybenzotriazole;

the preferred organic solvents are selected from the group consisting of $CH_2Cl_2$, $CHCl_3$, DMF and THF.

We have also discovered a process for the synthesis of peptidyl α-ketoamides with the structures
M—CO—$AA^2$—$AA^1$—CO—NH—R and
M—CO $AA^3$—$AA^2$—$AA^1$—CO—NH—R,
wherein M is selected from the group consisting of $C_{1-4}$ alkyl monosubstituted with phenyl, $C_{1-4}$ alkyl disubstituted with phenyl, $C_{1-4}$ alkyl monosubstituted with 1-naphthyl, $C_{1-4}$ alkyl monosubstituted with 2-naphthyl, $C_{1-4}$ alkoxy monosubstituted with phenyl, $C_{1-4}$ alkoxy disubstituted with phenyl, $Ar^1CH_2O$—, $Ar^1O$—, $Ar^1CH_2NH$—, $Ar^1NH$— and Heterocycle$^1$ $(CH_2)_q$—;

$Ar^1$ is selected from the group consisting of phenyl, phenyl monosubstituted with J, phenyl disubstituted with J, 1-naphthyl, 1-naphthyl monosubstituted with J, 2-naphthyl, and 2-naphthyl monosubstituted with J;

J is selected from the group consisting of halogen, OH, CN, $NO_2$, $NH_2$, COOH, $CO_2Me$, $CO_2Et$, $CF_3$, $C_{1-4}$ alkoxy, $C_{1-4}$ alkylamine, $C_2$-8 dialkylamine, $C_{1-4}$ perfluoroalkyl, and —$N(CH_2CH_2)_2O$;

Heterocycle$^1$ is selected from the group consisting of 2-furyl, 2-tetrahydrofuryl, 2-pyridyl, 3-pyridyl, 4-pyridyl, 2-pyrazinyl, 2-quinolinyl, 2-tetrahydroquinolinyl, 1-isoquinolinyl, 1-tetrahydroisoquinolinyl, and —$N(CH_2CH_2)_2O$;

q=0–2;

$AA^1$, $AA^2$ and $AA^3$ are side chain blocked or unblocked α-amino acids with the L configuration, D configuration, or DL configuration at the α-carbon selected independently from the group consisting of alanine, valine, leucine, isoleucine, histidine, proline, methionine, methionine sulfoxide, phenylalanine, serine, threonine, phenylglycine, norleucine, norvaline, arginine, lysine, tryptophan, glycine, cysteine, tyrosine, asparagine, glutamine, aspartic acid, glutamic acid, alpha-aminobutyric acid, O-methylserine, O-ethylserine, S-methylcysteine, S-ethylcysteine, S-benzylcysteine, $NH_2$—CH($CH_2CHEt_2$)—COOH, alpha-aminoheptanoic acid, $NH_2$—CH($CH_2$-cyclohexyl)—COOH, $NH_2$—CH($CH_2$-cyclopentyl)—COOH, $NH_2$—CH($CH_2$-cyclobutyl)—COOH, $NH_2$—CH($CH_2$-cyclopropyl)—COOH, $NH_2$—CH($CH_2$-1-naphthyl)—COOH, $NH_2$—CH($CH_2$-2-naphthyl)—COOH, 5,5,5-trifluoroleucine, and hexafluoroleucine;

R is selected from the group consisting of H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group substituted with K, $C_{1-10}$ alkyl with a morpholine [—$N(CH_2CH_2)O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4hydroxyphenyl), —NH—$CH_2CH_2$-(3-indolyl), $CH_2CH(OH)$—$Ar^2$ and $(CH_2)_n$-Heterocycle$^2$;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy—CO—, and $C_1$-10 alkyl—S—;

$Ar^2$ is selected from the group consisting of phenyl, phenyl monosubstituted with J, phenyl disubstituted with J, phenyl trisubstituted with J, pentafluorophenyl, $C_6H_4(3\text{-}OR^2)$, $C_6H_4(4\text{-}OR^2)$, $C_6H_3(3,4\text{-}(OR^2)_2$, $C_6H_2(2,4,6\text{-}(OR^2)_3$, 1-naphthyl, 1-naphthyl monosubstituted with J, 1-naphthyl disubstituted with J, 2-naphthyl, 2-naphthyl monosubstituted with J, 2-naphthyl disubstituted with J, 2-pyridyl, 2-quinolinyl, and 1-isoquinolinyl;

$R^2$ represents $C_{1-4}$ alkyl substituted with phenyl, phenyl and phenyl substituted with J.

Heterocycle$^2$ is selected from the group consisting of 2-furyl, 2-furyl monosubstituted with J, 2-tetrahydrofuryl, 2-pyridyl, 2-pyridyl monosubstituted with J, 3-pyridyl, 3-pyridyl monosubstituted with J, 4-pyridyl, 4-pyridyl monosubstituted with J, 2-pyrazinyl, 2-quinolinyl, 2-quinolinyl monosubstituted with J, 1-isoquinolinyl, 1-isoquinolinyl monosubstituted with J, 1-tetrahydroquinolinyl, 2-tetrahydroisoquinolinyl, 3-indolyl, 2-pyridyl-N-oxide, 3-pyridyl-N-oxide, 4-pyridyl-N-oxide, 2-(N-methyl-2-pyrrolyl), 1-imidazolyl, 1-pyrrolidinyl-2-one, 2-(5-methyl-3-thiazolyl), $(CH_2)_2$-NH-biotin;

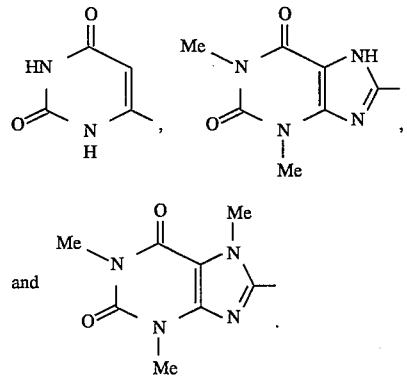

and consisting of treating a peptidyl α-enolester derived from a peptidyl α-ketoester with the structures
M—CO—$AA^2$—$AA^1$—$COOR^6$ and
M—CO—$AA^3$—$AA^2$—$AA^1$—$COOR^6$,
wherein
$R^6$ is selected from the group consisting of $C_{1-6}$ alkyls and $C_{1-6}$ alkyls monosubstituted with phenyl;
with a primary amine $RNH_2$ in an organic solvent at 0°–100° C. for 1–72 hours to give the desired peptidyl α-ketoamide, wherein
the preferred organic solvents are selected from the group consisting of $CH_2Cl_2$, EtOH, DMF and THF.

Representative Compounds

The following compounds are representatives of the invention:

Z-Leu-Abu-CONH—$(CH_2)_2OH$
Z-Leu-Abu-CONH—$(CH_2)_5OH$
Z-Leu-Abu-CONH—$(CH_2)_2O(CH_2)_2OH$
Z-Leu-Abu-CONH—$CH_2CH(OCH_3)_2$
Z-Leu-Abu-CONH—$CH_2CH(OC_2H_5)_2$
Z-Leu-Abu-CONH—$CH_2$-$C_6H_8[1,3,3\text{-}(CH_3)_3\text{-}5\text{-}OH]$
Z-Leu-Abu-CONH—$(CH_2)_2C_6H_4(4\text{-}OH)$
Z-Leu-Abu-CONH—$(CH_2)_2C_6H_4(2\text{-}OCH_3)$
Z-Leu-Abu-CONH—$(CH_2)_2C_6H_4(3\text{-}OCH_3)$
Z-Leu-Abu-CONH—$(CH_2)_2C_6H_4(4\text{-}OCH_3)$
Z-Leu-Abu-CONH—$CH_2C_6H_3[3,5\text{-}(OCH_3)_2]$
Z-Leu-Abu-CONH—$CH_2CH(OH)Ph$
Z-Leu-Abu-CONH—$CH_2CH(OH)C_6H_4(4\text{-}OCH_3)$ Z-Leu-Abu-CONH—CH$_2$CH(OH)C$_6$H$_2$[2,4,6-(OCH$_3$)$_3$]
Z-Leu-Abu-CONH—CH$_2$CH(OH)C$_6$H$_4$[4-N(CH$_3$)$_2$]
Z-Leu-Abu-CONH—CH$_2$CH(OH)C$_6$F$_5$
Z-Leu-Abu-CONH—CH$_2$CH(OH)C$_6$H$_4$(3-CF$_3$)
Z-Leu-Abu-COOH-CH$_2$CH(OH)C$_6$H$_4$(3OPh)
Z-Leu-Abu-CONH—CH$_2$CH(OH)C$_6$H$_4$(4-OPh)
Z-Leu-Abu-CONH—CH$_2$CH(OH)C$_6$H$_4$(4-OCH$_2$Ph)
Z-Leu-Abu-CONH—CH$_2$CH(OH)C$_6$H$_4$-3-OC$_6$H$_4$(3-CF$_3$ )
Z-Leu-Abu-CONH—CH$_2$CH(OH)C$_6$H$_4$-3-OC$_6$H$_3$(3,4-Cl$_2$)
Z-Leu-Abu-CONH—CH$_2$CH(OH)C$_6$H$_3$[3,4-(OCH$_2$ Ph)$_2$]
Z-Leu-Abu-CONH—CH$_2$CH(OH)-1-C$_{10}$H$_7$
Z-Leu-Abu-CONH—CH$_2$CH(OH)-2-C$_{10}$H$_7$
Z-Leu-Phe-CONH—CH$_2$CH(OH)Ph
Z-Leu-Phe-CONH—CH$_2$CH(OH)C$_6$H$_4$[4-N(CH$_3$)$_2$]
Z-Leu-Phe-CONH—CH$_2$CH(OH)C$_6$F$_5$
Z-Leu-Phe-CONH—CH$_2$CH(OH)C$_6$H$_4$(3-CF$_3$)
Z-Leu-Phe-CONH—CH$_2$CH(OH)C$_6$H$_4$(3-OPh)
Z-Leu-Phe-CONH—CH$_2$CH(OH)C$_6$H$_4$(4-OPh)
Z-Leu-Phe-CONH—CH$_2$CH(OH)C$_6$H$_4$(4-OCH$_2$Ph)
Z-Leu-Phe-CONH—CH$_2$CH(OH)C$_6$H$_4$-3-OC$_6$H$_4$(3-CF$_3$)
Z-Leu-Phe-CONH—CH$_2$CH(OH)C$_6$H$_4$-3-OC$_6$H$_3$(3,4-Cl$_2$)
Z-Leu-Phe-CONH—CH$_2$CH(OH)C$_6$H$_3$(3,4-(OCH$_2$Ph)$_2$)
Z-Leu-Abu-CONH—CH$_2$-2-furyl
Z-Leu-Abu-CONH—CH$_2$-2-tetrahydrofuryl
Z-Leu-Abu-CONH—CH$_2$-2-pyridyl
Z-Leu-Abu-CONH—CH$_2$-3-pyridyl
Z-Leu-Abu-CONH—CH$_2$-4-pyridyl
Z-Leu-Abu-CONH—(CH$_2$)$_2$-2-pyridyl
Z-Leu-Abu-CONH—CH$_2$-2-pyridyl(3—COOCH$_3$)
Z-Leu-Abu-CONH—CH$_2$-2-pyridyl(5—COOCH$_3$)
Z-Leu-Abu-CONH—(CH$_2$)$_2$-2-(N-methylpyrrolyl)
Z-Leu-Abu-CONH—(CH$_2$)$_3$-1-imidazolyl
Z-Leu-Abu-CONH—(CH$_2$)$_2$-4-morpholinyl
Z-Leu-Abu-CONH—(CH$_2$)$_3$-4-morpholinyl
Z-Leu-Abu-CONH—(CH$_2$)$_3$-1-pyrrolidinyl-2-one
Z-Leu-Abu-CONH—CH$_2$)$_2$-3-indolyl
Z-Leu-Abu-CONH—CH$_2$-2-quinolinyl
Z-Leu-Abu-CONH—CH$_2$-1-isoquinoline
Z-Leu-Abu-CONH—(CH$_2$)$_3$-1-tetrahydroquinolinyl
Z-Leu-Abu-CONH—(CH$_2$)3-2-tetrahydroisoquinolinyl
Z-Leu-Abu-CONH—CH$_2$-8-caffeinyl
Z-Leu-Abu-CONH—CH$_2$-2-(4-methyl-2-thiazolyl)
Z-Leu-Abu-CONH-CONH—(CH$_2$)$_2$NH-biotinyl
Z-Leu-Abu-CONH—CH$_2$-3-pyridyl-N-oxide
Z-Leu-Abu-CONH—CH$_2$-6-uracil
Z-Leu-Phe-CONH—CH$_2$-2-pyridyl
Z-Leu-Phe-CONH—(CH$_2$)$_3$-4-morpholinyl
Z-Leu-Phe-CONH—CH$_2$-2-quinolinyl
Z-Leu-Phe-CONH—CH$_2$-1-isoquinolinyl 15
Z-Leu-Phe-CONH—(CH$_2$)$_3$-1-tetrahydroquinolinyl
Z-Leu-Phe-CONH-(CH$_2$)$_3$-2-tetrahydroisoquinolinyl
Z-Leu-Phe-CONH—(CH$_2$)$_2$-NH-biotinyl
Z-Leu-Nva-CONH—CH$_2$CH(OH)Ph
Z-Leu-Nva-CONH—CH$_2$-2-pyridyl
Z-Leu-Nva-CONH—(CH$_2$)$_3$-4-morpholinyl
   CH$_3$OCO(CH$_2$)$_2$CO-Leu-Abu-CONHEt
2-furyl-CO-Leu-Abu-CONHEt
2-tetrahydrofuryl-CO-Leu-Abu-CONHEt
3-pyridyl-CO-Leu-Abu-CONHEt
2-pyrazyl-CO-Leu-Abu-CONHEt
2-quinolinyl-CO-Leu -Abu-CONHEt
1-isoquinolinyl-CO-Leu-Abu-CONHEt
4-morpholinyl-CO-Leu-Abu-CONHEt
Ph(CH$_2$)2CO-Leu-Abu-CONHEt
1-C$_{10}$H$_7$CH$_2$CO-Leu-Abu-CONHEt
Ph$_2$CHCO-Leu -Abu-CONHEt
Ph$_2$CHCO-Leu-Abu-CONH—CH$_2$CH(OH)Ph
Ph$_2$CHCO-Leu-Abu-CONH—CH$_2$-2-pyridyl
Ph$_2$CHCO-Leu-Abu-CONH—(CH$_2$)$_3$-4-morpholinyl
Ph$_2$CHCO-Leu-Phe-CONH—CH$_2$CH(OH)Ph
Ph$_2$CHCO-Leu-Phe-CONH—CH$_2$-2-pyridyl
Ph$_2$CHCO-Leu-Phe-CONH—(CH$_2$)$_3$-4-morpholinyl

Materials and Experimental Methods

HEPES, heparin, and A23187 were obtained from Calbiochem. Suc-Leu-Tyr-AMC and chromogenic substrates were obtained from Sigma. Calpain I was purified from human erythrocytes according to the method of Kitahara (Kitahara et al., *J. Biochem.* 95, 1759–1766) omitting the Blue-Sepharose step. Calpain II from rabbit muscle and cathepsin B were purchased from Sigma. Papain was purchased from Calbiochem.

Assay of inhibitory Potency.

Peptide α-ketoamides were assayed as reversible enzyme inhibitors. Various concentrations of inhibitors in Me$_2$SO were added to the assay mixture which contained buffer and substrate. The reaction was started by the addition of the enzyme and the hydrolysis rates were followed spectrophotometrically or fluorimetrically.

Calpain I from human erythrocytes and calpain II from rabbit were assayed using Suc-Leu-Tyr-AMC [Sasaki et al., *J. Biol. Chem.* 259, 12489–12494 (1984); incorporated herein by reference], and the AMC (7-amino-4-methylcoumarin) release was followed fluorimetrically (excitation at 380 nm, and emmision at 460 nm). Calpains were assayed in 25 mM Tris pH=8.0, 10 mM CaC$_{12}$. Fluorescence was followed using a Gilson FL-1A fluorometer or a Perkin-Elmer 203 Fluorescence spectrometer. Cathepsin B was assayed in 20 mM sodium acetate pH=5.2, 0.5 mM dithiothreitol using Bz-Phe-Val-Arg-p-nitroanilide as substrate. Alternately, cathepsin B was assayed with Z-Arg-Arg-AFC [Barrett and Kirschke, *Methods Enzymol.* 80, 535–561 (1981); incorporated herein by reference], and the AFC (7-amino-4-trifluoromethylcoumarin) release was followed fluorimetrically (excitation at 400 nm and emmision at 505 nm). Papain was assayed in 100 mM KPO$_4$, 1 mM EDTA, 2.5 mM cysteine pH=6.0 using Bz-Arg-AMC or Bz-Arg-NA [Kanaoka et al., *Chem. Pharm. Bull.* 25, 3126–3128 (1977); incorporated herein by reference] as a substrate. The AMC (7-amino-4-methylcoumarin) release was followed fluorimetrically (excitation at 380 nm, and emmision at 460 nm). Enzymatic hydrolysis rates were measured at various substrate and inhibitor concentrations, and K$_I$ values were determined by either Lineweaver-Burk plots or Dixon plots.

A 0.1M Hepes, 0.5M NaCl, pH 7.5 buffer was utilized for human leukocyte elastase (HLE), porcine pancreatic elastase (PPE), chymotrypsin and cathepsin G. A 0.1 Hepes, 0.01 M CaCl$_2$, pH 7.5 buffer was utilized for trypsin, plasmin, and coagulation enzymes. A 50 mM Tris.HCl, 2 mM EDTA, 5 mM cysteine, pH 7.5 was used as a buffer for papain. A 88 mM KH$_2$PO$_4$, 12 mM Na$_2$HPO$_4$, 1.33 mM EDTA, 2.7 mM cysteine, pH 6.0 solution was used as a buffer for cathepsin B. A 20 mM Hepes, 10 mM CaCl$_2$, 10 mM mercatoethanol, pH 7.2 buffer was utilized for calpain I and calpain II.

HLE and PPE were assayed with MeO-Suc-Ala-Ala-Pro-Val-NA and Suc-Ala-Ala-Ala-NA, respectively [Nakajima et al., *J. Biol. Chem.* 254, 4027–4032 (1979); incorporated herein by reference]. Human leukocyte cathepsin G and chymotrypsin A$_\alpha$ were assayed with Suc-Val-Pro-Phe-NA [Tanaka et al., *Biochemistry* 24, 2040–2047 (1985); incorporated herein by reference]. The hydrolysis of peptide 4-nitroanilides was measured at 410 nm [ε$_{410}$=8800 M$^{-1}$cm$^-$1; Erlanger et al., *Arch. Biochem. Biophys.* 95, pp 271–278

(1961); incorporated herein by reference]. Trypsin, thrombin, human plasma kallikrein, porcine pancreatic kallikrein, human factor XIa, and human plasmin were assayed with Z-Arg-SBzl or Z-Gly-Arg-SBu-i [McRae et al., *Biochemistry* 20, 7196–7206 (1981); incorporated herein by reference]. All peptide thioester hydrolysis rates were measured with assay mixtures containing 4,4'-dithiodipyridine [$\epsilon_{324}$= 19800 $M^{-1}cm^{-1}$; Grasetti & Murray, *Arch. Biochem. Biophys.* 119, 41–49 (1967); incorporated herein by reference].

Structure-Activity Relationships

Table 1 shows the inhibition constants ($K_I$) for calpain I, calpain II and cathepsin B. Changing the R group on the amide significantly improves the inhibitory potency toward calpains. Dipeptide α-ketoamides with Abu, Phe, and Nva in the $P_1$ site and Leu in the $P_2$ site are potent inhibitors of these cysteine proteases. The presence of a hydrogen bond donor in the $S_1'$ subsite of the cysteine proteases which may be interacting with the N-H on the ketoamide functional group is indicated since disubstituted amides were much less effective inhibitors. Derivatives of Z-Leu—AA—CONHR where the R group contained a hydroxy or alkoxy group, such as $(CH_2)_5OH$ and $CH_2CH(OC_2H_5)_2$, are very good inhibitors of the calpains. The prescence of an aromatic group in $P_1'$ position of the peptide ketoamide inhibitor resulted in improved inhibitory potency for calpains which indicates the prescence of hydrophobic residues in the S' subsites of both calpains. The derivatives Z-Leu—AA—CONH$(CH_2)_n$R where R was phenyl, phenyl substituted with hydroxy or alkoxy groups and naphthyl, are also very good inhibitors of calpains and cathepsin B. Derivatives of Z-Leu-Abu-CONH$(CH_2)_n$R where the R group contained a heterocylic group which has both a hydrophobic moiety with an electronnegative atom, are among the best inhibitors for calpains and cathepsin B. For example Z-Leu-NvaCONHCH$_2$-2-pyridyl is the best inhibitor of calpain I. Z-Leu-Abu-CONHCH$_2$-2-pyridyl is the best inhibitor of calpain II respectively in this series, but its isomers, Z-Leu-Abu-CONH—CH$_2$-3-pyridyl and Z-Leu-Abu-CONH—CH$_2$-4-pyridyl, are substantially poorer inhibitors.

TABLE 1

Inhibition of Cysteine Proteases by Peptide α-Ketoamides with the Structures Z-Leu—AA—CONHR.

| | $K_I$ (μM) | | |
|---|---|---|---|
| R | Cal I | Cal II | Cat B |
| AA = α-aminobutyric acid | | | |
| $(CH_2)_2OH$ | 0.8 | 0.078 | 4.5 |
| $(CH_2)_5OH$ | 0.5 | 0.051 | 0.28 |
| $(CH_2)_2O(CH_2)_2OH$ | 0.65 | 0.16 | 2.0 |
| $CH_2CH(OCH_3)_2$ | 0.5 | | |
| $CH_2CH(OC_2H_5)_2$ | 0.2 | | |
| $CH_2$—$C_6H_8$(1,3,3-$(CH_3)_3$-5-OH) | 0.42 | 0.069 | 0.89 |
| $(CH_2)_2C_6H_4$(4-OH) | 0.38 | 0.06 | |
| $(CH_2)_2C_6H_4$(2-OCH$_3$) | 0.13 | 0.16 | 0.63 |
| $(CH_2)_2C_6H_4$(3-OCH$_3$) | 0.11 | 0.086 | 0.31 |
| $(CH_2)_2C_6H_4$(4-OCH$_3$) | 0.12 | 0.046 | 0.44 |
| $CH_2C_6H_3$(3,5-(OCH$_3$)$_2$) | 2.3 | 0.022 | 1.8 |
| $CH_2$-2-furyl | 0.80 | 0.033 | 6.0 |
| $CH_2$-2-tetrahydrofuryl | 0.33 | 0.066 | 4.5 |
| $CH_2$-2-pyridyl | 0.64 | 0.017 | 3.0 |
| $CH_2$-3-pyridyl | | 0.12 | 1.2 |
| $CH_2$-4-pyridyl | 1.1 | 0.11 | 6.4 |
| $(CH_2)_2$-2-pyridyl | 0.41 | 0.47 | 0.20 |
| $CH_2$-2-pyridyl(3-COOCH$_3$) | ca.110 | | |
| $CH_2$-2-pyridyl(5-COOCH$_3$) | ca.28 | | |

TABLE 1-continued

Inhibition of Cysteine Proteases by Peptide α-Ketoamides with the Structures Z-Leu—AA—CONHR.

| | $K_I$ (μM) | | |
|---|---|---|---|
| R | Cal I | Cal II | Cat B |
| $(CH_2)_2$-2-(N-methylpyrrole) | 0.16 | 0.076 | 1.2 |
| $(CH_2)_3$-1-imidazolyl | 0.29 | 0.068 | 9.9 |
| $(CH_2)_2$-4-morpholinyl | 1.0 | 0.16 | 2.5 |
| $(CH_2)_3$-4-morpholinyl | 0.14 | 0.041 | 6.9 |
| $(CH_2)_3$-1-pyrrolidine-2-one | 1.2 | 0.27 | 2.0 |
| $(CH_2)_2$-3-indolyl | 0.3 | 0.05 | |
| $CH_2$-2-quinolinyl | 0.13 | | |
| $CH_2$-1-isoquinolinyl | 0.25 | | 0.3 |
| $(CH_2)_3$-1-tetrahydroquinolinyl | 0.37 | | |
| $(CH_2)_3$-2-tetrahydroisoquinolinyl | 0.31 | | 8 |
| $CH_2$-8-caffeine | 32.0 | | |
| $CH_2$-2-(4-methylthiazole) | 34.0 | | |
| $(CH_2)_2$NH-biotinyl | 0.65 | | |
| $CH_2$-3-pyridyl-N-oxide | 9.5 | | |
| $CH_2$-6-uracil | 9.0 | | |
| AA = phenylalanine | | | |
| $CH_2$-2-pyridyl | | 0.65 | 0.27 |
| $(CH_2)_3$-4-morpholinyl | 0.22 | | |
| $CH_2$-2-quinolinyl | 0.11 | 0.023 | 0.34 |
| $CH_2$-1-isoquinolinyl | 2.4 | | 9.6 |
| $(CH_2)_3$-1-tetrahydroquinolinyl | 0.38 | | |
| $(CH_2)_3$-2-tetrahydroisoquinolinyl | 0.22 | | |
| $(CH_2)_2$NH-biotinyl | 0.22 | | |
| AA = Norvaline | | | |
| $CH_2$-2-pyridyl | 0.019 | 0.12 | |
| $(CH_2)_3$-4-morpholinyl | 0.25 | 0.10 | 4.2 |

Table 2 shows the inhibition constants ($K_I$) of Z-Leu—AA—CONH—CH$_2$CH(OH)R. The hydrophobic moiety substituted with CH$_2$CH—X (X=electronegative atoms such as O, N) resulted in good inhibitor structures. Z-Leu-Abu-CONH—CH$_2$CH(OH)C$_6$F$_5$ is the best inhibitor for calpain I, and Z-Leu-Abu-CONH—CH$_2$CH(OH)Ph is the best inhibitor for calpain II respectively in this series.

TABLE 2

Inhibition of Cysteine Proteases by Peptide α-Ketoamides with the Structures Z-Leu—AA—CONH—CH$_2$CH(OH)-R.

| | $K_I$ (μM) | | |
|---|---|---|---|
| R | Cal I | Cal II | Cat B |
| AA = α-aminobutyric acid | | | |
| Ph | 1.1 | 0.015 | 0.37 |
| $C_6H_4$(4-OCH$_3$) | 0.24 | | |
| $C_6H_2$(2,4,6-(OCH$_3$)$_3$) | 0.38 | | |
| $C_6H_4$(4-N(CH$_3$)$_2$) | 0.33 | | |
| $C_6F_5$ | 0.05 | | |
| $C_6H_4$(3-CF$_3$) | 0.35 | | |
| $C_6H_4$(3-OPh) | 0.90 | | |
| $C_6H_4$(4-OPh) | 0.10 | | |
| $C_6H_4$(4-OCH$_2$Ph) | 0.08 | | |
| $C_6H_4$-3-OC$_6$H$_4$(3-CF$_3$) | 0.07 | | |
| $C_6H_4$-3-OC$_6$H$_3$(3,4-Cl$_2$) | 0.27 | | |
| $C_6H_3$(3,4-(OCH$_2$Ph)$_2$) | 0.23 | | |
| 1-$C_{10}H_7$ | 0.12 | | |
| 2-$C_{10}H_7$ | 0.35 | | |
| AA = phenylalanine | | | |
| Ph | 1.3 | 0.05 | 2.1 |
| $C_6H_4$(4-N(CH$_3$)$_2$) | 0.62 | | |
| $C_6F_5$ | 0.70 | | |
| $C_6H_4$(3-CF$_3$) | 0.46 | | |
| $C_6H_4$(3-OPh) | 0.60 | | |

TABLE 2-continued

Inhibition of Cysteine Proteases by Peptide α-Ketoamides
with the Structures Z-Leu—AA—CONH—CH$_2$CH(OH)-R.

| | $K_I$ (μM) | | |
|---|---|---|---|
| R | Cal I | Cal II | Cat B |
| C$_6$H$_4$(4-OPh) | 0.20 | | |
| C$_6$H$_4$(4-OCH$_2$Ph) | 0.20 | | |
| C$_6$H$_4$-3-OC$_6$H$_4$(3-CF$_3$) | 0.18 | | |
| C$_6$H$_4$-3-OC$_6$H$_3$(3,4-Cl$_2$) | 0.59 | | |
| C$_6$H$_3$(3,4-(OCH$_2$Ph)$_2$) | | | |
| AA = Norvaline | | | |
| Ph | 7.8 | 11 | |

In general, replacement of the Z group (PhCH$_2$OCO—) by related aromatic groups also resulted in good inhibitor structures (Table 3).

TABLE 3

Inhibition of Cysteine Proteases by Peptide α-ketoamides
with the Structures M$_1$CO-Leu—AA—CONH-R.

| | | $K_I$ (μM) | | |
|---|---|---|---|---|
| M$_1$ | R | Cal I | Cal II | Cat B |
| AA = α-aminobutyric acid | | | | |
| Z | Et | 0.5 | 0.23 | 2.4 |
| CH$_3$OCO(CH$_2$)$_2$ | Et | 3.8 | | |
| 2-furyl | Et | 0.85 | | |
| 2-tetrahydrofuryl | Et | 18.5 | | |
| 3-pyridyl | Et | 1.30 | | |
| 2-pyrazinyl | Et | 0.30 | | |
| 2-quinolinyl | Et | 0.5 | | |
| 1-isoquinolinyl | Et | 0.35 | | |
| 4-morpholinyl | Et | 7.9 | | |
| Ph(CH$_2$)$_2$ | Et | | | |
| 1-C$_{10}$H$_7$CH$_2$ | Et | | | |
| Ph$_2$CH | Et | 5.0 | | |
| Ph$_2$CH | CH$_2$CH(OH)Ph | 0.75 | 0.20 | |
| Ph$_2$CH | CH$_2$-2-pyridyl | 0.5 | 0.09 | 2.8 |
| Ph$_2$CH | (CH$_2$)$_3$-4-morpholinyl | 0.8 | 0.11 | 2.3 |
| AA = phenylalanine | | | | |
| Ph$_2$CH | CH$_2$CH(OH)Ph | 10 | 0.73 | |
| Ph$_2$CH | CH$_2$-2-pyridyl | 1.1 | 0.36 | 2.2 |
| Ph$_2$CH | (CH$_2$)$_3$-4-morpholinyl | 0.76 | 0.074 | 3.8 |

Table 4 shows the inhibition constants (IC$_{50}$), for human leuckocyte elastase (HLE) and cathepsin G (Cat G). Dipeptidyl α-ketoamides with Abu and Phe in the P$_1$ site are potent inhibitors of HLE.

TABLE 4

Inhibition of Serine Proteases by Peptide α-ketoamides the
Structures Z-Leu—AA—CONH-R.

| | IC$_{50}$(μM) | |
|---|---|---|
| R | HLE | Cat G |
| AA = α-aminobutyric acid | | |
| H | >120 | NI |
| n-Pr | >120 | >217 |
| n-Bu | 63 | 148 |
| i-Bu | 78 | 134 |
| C$_7$H$_{15}$ | 52 | >116 |
| C$_8$H$_{17}$ | 45 | >217 |
| C$_9$H$_{19}$ | 78 | 150 |

TABLE 4-continued

Inhibition of Serine Proteases by Peptide α-ketoamides the
Structures Z-Leu—AA—CONH-R.

| | IC$_{50}$(μM) | |
|---|---|---|
| R | HLE | Cat G |
| C$_{10}$H$_{21}$ | 47 | 162 |
| CH$_2$CH(OH)—C$_6$H$_4$(4-OCH$_3$) | 32 | |
| CH$_2$CH(OH)—C$_6$H$_4$(4-N(CH$_3$)$_2$) | 18 | >204 |
| | ($K_I$ = 19) | |
| CH$_2$CH(OH)—C$_6$F$_5$ | 44 | |
| CH$_2$CH(OH)—C$_6$H$_4$(3-CF$_3$) | 11 | >204 |
| | ($K_I$ = 9) | |
| C$_6$H$_4$(3-OPh) | 45 | |
| C$_6$H$_4$(4-OPh) | 28 | |
| CH$_2$CH(OH)—C$_6$H$_4$(4-OCH$_2$Ph) | 18 | >102 |
| | ($K_I$ = 15) | |
| CH$_2$CH(OH)—C$_6$H$_4$-3-OC$_6$H$_4$(3-CF$_3$) | 30 | |
| C$_6$H$_3$(3,4-(OCH$_2$Ph)$_2$) | 64 | |
| CH$_2$-2-furyl | 38 | |
| (CH$_2$)$_3$-4-morpholinyl | >217 | |
| (CH$_2$)$_2$-3-indolyl | 48 | |
| CH$_2$-8-caffeine | 156 | |
| (CH$_2$)$_2$NH-biotinyl | 38 | |
| AA = phenylalanine | | |
| H | 100 | 80 |
| Et | 74 | 91 |
| n-Pr | 44 | 65 |
| n-Bu | 16 | 68 |
| | ($K_I$ = 11) | ($K_I$ = 4.9) |
| i-Bu | 20 | 45 |
| | ($K_I$ = 10) | ($K_I$ = 21) |
| sec-Bu | 50 | 128 |
| CH$_2$Ph | 40 | 63 |
| (CH$_2$)$_2$Ph | 24 | 112 |
| CH$_2$CH(OH)—Ph | 44 | 102 |
| C$_6$H$_4$(4-N(CH$_3$)$_2$) | 28 | 58 |
| C$_6$F$_5$ | | |
| C$_6$H$_4$(3-CF$_3$) | | |
| C$_6$H$_4$(3-OPh) | | |
| C$_6$H$_4$(4-OPh) | 32 | >102 |
| C$_6$H$_4$(4-OCH$_2$Ph) | 40 | 58 |
| C$_6$H$_4$-3-OC$_6$H$_4$(3-CF$_3$) | 70 | 80 |
| C$_6$H$_4$-3-OC$_6$H$_3$(3,4-Cl$_2$) | | |
| C$_6$H$_3$(3,4-(OCH$_2$Ph)$_2$) | 22 | 66 |
| (CH$_2$)$_3$-4-morpholinyl | >222 | 136 |

Inhibition Mechanism.

A crystal structure of one α-ketoester bound into the active site of porcine pancreatic elastase has been completed and a schematic drawing of the interactions observed is shown below. The active site Set-195 oxygen of the enzyme has added to the carbonyl group of the ketoester to form a tetrahedral intermediate which is stabilized by interactions with the oxyanion hole. This structure resembles the tetrahedral intermediate involved in peptide bond hydrolysis and proves that α-ketoester are transition-state analogs. His-57 is hydrogen bonded to the carbonyl group of the ester functional group, the peptide backbone on a section of PPE's backbone hydrogen bonds to the inhibitor to form a β-sheet, and the benzyl amide is directed toward the S' subsites. The side chain of the P$_1$ amino acid residue is located in the S$_1$ pocket of the enzyme. Interactions with ketoamides would be similar except for that there would be the possibility of forming an additional hydrogen bond with the NH group of the ketoamide functional group. If R is longer substutuent, then they would make favorable interactions with the S' subsites of the enzyme.

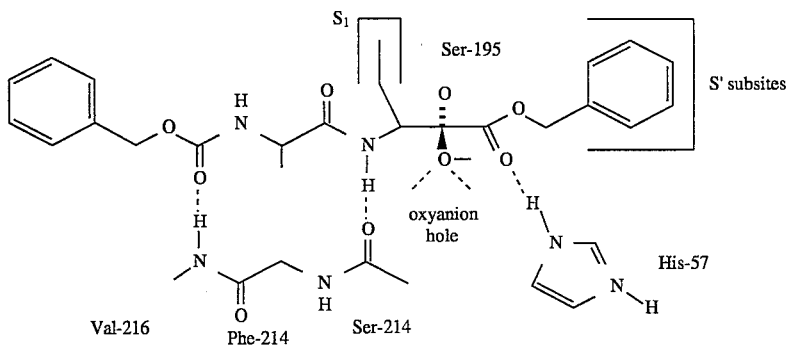

The active site of cysteine proteases share several features in common with serine proteases including an active site histidine residue. In place of the Ser-195, cysteine proteases have an active site cysteine residue which would add to the ketonic carbonyl group of the peptide ketoamides to form an adduct very similar to the structure depicted above except with a cysteine residue replacing the serine-195 residue. Additional interactions would occur between the extended substrate binding site of the cysteine protease and the inhibitor which would increase the binding affinity and specificity of the inhibitors.

Inhibitor Design and Selection.

The peptide α-ketoamide derivatives, as shown in the above crystal structure, bind to the enzymes using many of the interactions that are found in complexes of a particular individual enzyme with its substrates. In order to design an inhibitor for a particular serine or cysteine protease, it is necessary to: 1) find the amino acid sequences of good peptide substrates for that enzyme, and 2) place those or similar amino acid sequences into a α-ketoamide structure. Additional interactions with the enzyme can be obtained by tailoring the R group of the inhibitor to imitate the amino acid residues which are preferred by an individual protease at the $S_1'$ and $S_2'$ subsites. For example, ketoamides with R=alkyl substituted with phenyl would interact effectively with serine and cysteine proteases which prefer Phe, Tyr, Trp residues at $P_1'$ and/or $P_2'$. Likewise, the $M_1$ group can be tailored to interact with the S subsites of the enzyme. This design strategy will also work when other classes of peptide inhibitors are used in place of the peptide substrate to gain information on the appropriate sequence to place in the ketoamide inhibitor. Thus, we are able to predict the structure of new inhibitors for other serine and cysteine proteases based on knowledge of their substrate specificities. Once a good inhibitor structure for a particular enzyme is found, it is then possible to change other characteristics such as solubility or hydrophobicity by adding substituents to the $M_1$ or R groups.

Suc-Phe-Leu-Phe-NA is an excellent substrate for chymotrypsin, cathepsin G, and most cell chymases. Thus, the corresponding α-ketoamide will be an excellent inhibitor for these chymotrypsin-like enzymes. In the case of the cysteine protease calpain, a good inhibitor sequence is Ac-Leu-Leu-Nle-H. We have found that Ketoamides, related in structure such as Z-Leu-Abu-CO—NHR and Z-Leu-Phe-CO—NHR are potent inhibitors for calpain.

In Vitro Uses.

To use the above inhibitors in vitro, they are dissolved in an organic solvent such as dimethylsulfoxide or ethanol, and are added to an aqueous solution containing cysteine proteases. The final concentration of the organic solvent should be less than 25%. The inhibitors may also be added as solids or in suspension. The cysteine protease inhibitors of this invention would be useful in a variety of experimental procedures where proteolysis is a significant problem. Inclusion of these inhibitors in a radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast and human cells to yield a purified cloned product in higher yield.

The novel compounds of this invention are effective in the prevention of unnecessary proteolysis caused by chymotrypsin-like and elastase-like enzymes in the process of purification, transport and storage of peptides and proteins as shown in Tables I, II, III, and IV by effective inhibition of chymotrypsin, elastase, and cysteine proteases.

In Vivo Uses.

Peptide α-ketoamide can be used to control protein turnover, muscular dystrophy, myocardial tissue damage, tumor metastasis, and bone resorption as shown in Table I, II, and III by effective inhibition of lysosomal cathepsin B. Peptide α-ketoamides can also be used as neuroprotectants or for the treatment of ischemia, stroke, restenosis or Alzheimer's disease as shown in Table I, II, and III by effective inhibiton of calpain I and calpain II.

Considerable evidence has shown that leukocyte elastase and/or related enzymes play a role in tumor cell metastasis [Salo et al., Int. J. Cancer 30, pp 669–673 (1973); Kao et al., Biochem. Biophys. Res. Comm. 105, pp 383–389 (1982); Powers, J. C. in Modification of Proteins, R. E. Feeney and J. R. Whitaker, eds., Adv. Chem. Set 198, Amer. Chem. Soc., Wash., D.C. pp 347–367 (1982); all incorporated herein by reference], therefore it is suggested that compounds of this invention may have anti-tumor activity.

Pulmonary emphysema is a disease characterized by progressive loss of lung elasticity due to the destruction of lung elastin and alveoli. The destructive changes of lung parentchyma associated with pulmonary emphysema are caused by uncontrolled proteolysis in lung tissues [Janoff, Chest 83, 54–58 (1983); incorporated herein by reference]. A number of proteases have been shown to induce emphysema in animals [Marco et al., Am. Rev. Respir. Dis. 104, 595–598 (1971); Kaplan, J. Lab. Clin. Med. 82, 349–356 (1973); incorporated herein by reference], particularly human leukocyte elastase [Janoff, ibid 115, 461–478 (1977); incorporated herein by reference]. Leukocyte elastase and other mediators of inflammation also appear to play a role in diseases such as mucocutaneous lymph node syndrome [Reiger et al., Eur. J. Pediatr. 140, 92–97 (1983); incorporated herein by reference] and adult respiratory distress syndrome [Stockley, Clinical Science 64, 119–126 (1983);

Lee et al., *N. Eng. J. Med.* 304, 192–196 (1981);Rinaldo, ibid 301,900–909 (1982); incorporated herein by reference].

It is known that in vitro activity of elastase inhibitors correlates with in vivo activity in animal models of emphysema and inflammation [Otterness et al., editors, Advances in Inflammation Research, Vol. 11, Raven Press 1986; incorporated herein by reference]. Prophylactic administration of an inhibitor of elastase significantly diminishes the extent of elastase-induced emphysema [Kleinerman et al., *Am. Rev. Resir. Dis.* 12 1,381–387 (1980); Lucey et al., *Eur. Respir. J.* 2,421–427 (1989); incorporated herein by reference]. Thus the novel inhibitors described here should be useful for the treatment of emphysema and inflammation. Elastase inhibitors have been used orally, by injection, or by instillation in the lungs in animal studies (Powers, *Am. Rev. Respir. Dis.*, 127, s54-s58 (1983); Powers and. Bengali, *Am. Rev. Respir. Dis.* 134, 1097–1100 (1986); these two articles are incorporated herein by reference). The inhibitors described above can be used by any of these routes.

Drug Delivery.

For therapeutic use, the peptide α-ketoamides may be administered orally, topically or parenterally. The term parenteral as used includes subcutaneous injection, intravenous, intramuscular, intrasternal injection or infusion techniques. The dosage depends primarily on the specific formulation and on the object of the therapy or prophylaxis. The amount of the individual doses as well as the administration is best determined by individually assessing the particular case.

The pharmaceutical compositions containing the active ingredient may be in a form suitable for oral use, for example as tablets, troches, lozenges, aqueous or oily suspensions, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the peptide α-ketoamides or their pharmaceutically acceptable salts will normally be in the dosage range from 0.2 to 140 mg/kg of body weight. Administration is made by intravenous, intramuscular or subcutaneous injection. Accordingly, pharmaceutical compositions for parenteral administration will contain in a single dosage form about 10 mg to 7 gms of the compounds per dose. In addition to the active ingredient, these pharmaceutical compositions will usually contain a buffer, e.g. a phosphate buffer which keeps the pH in the range from 3.5 to 7 and also sodium chloride, mannitol or sorbitol for adjusting the isotonic pressure.

A composition for topical application can be formulated as an aqueous solution, lotion, jelly or an oily solution or suspension. A composition in the form of an aqueous solution is obtained by dissolving the compounds of this invention in aqueous buffer solution of pH 4 to 6.5 and if desired, adding a polymeric binder. An oily formulation for topical application is obtained by suspending the compounds of this invention in an oil, optionally with the addition of a swelling agent such as aluminium stearate and/or a surfactant.

SYNTHETIC METHODS

The α-ketoamide inhibitors are prepared from the corresponding α-ketoesters. The α-ketoester are prepared by a two step Dakin-West reaction from the corresponding peptide acid as shown in the following scheme (Charles et al., *J. Chem. Soc. Perkin 1*, 1139–1146, 1980).

The precursor peptide can be prepared using standard peptide chemistry which is well described in publications such as *The Peptides, Analysis, Synthesis, Biology*, Vol. 1–9, published in 1979–1987 by Academic Press and Houben-Weyl Methoden der Organischen Chemie, Vol. 15, Parts 1 and 2, *Synthese von Peptiden*, published by Georg Thieme Verlag, Stuttgart in 1974 (both references incorporated herein by reference).

The $M_1CO$— group can be introduced using a number of different reaction schemes. For example it could be introduced directly on an amino acid as shown in the following scheme (top), or the $M_1CO$— group could be introduced by reaction with an amino acid ester, followed by removal of the ester group to give the same product (middle), or the $M_1CO$— group could be introduced by deblocking Z group from ketoamide then reaction with an acid or chloride (bottom).

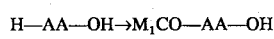

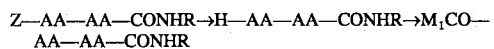

The techniques for introduction of the $M_1CO$ group is well documented in the The Peptides, Houben-Weyl, and many other textbooks on organic synthesis. The $M_1CO$—AA—AA—OH derivatives could then be used directly in the Dakin-West reaction. The R group in the ketoester structures is introduced during the Dakin-West reaction by reaction with an oxalyl chloride Cl—CO—CO—O—R.

Ketoamides $M_1CO$—AA—AA—CONHR were prepared indirectly from the ketoesters. The ketone carbonyl group is first protected as shown in the following scheme and then the ketoamide is prepared by reaction with an amine $RNH_2$. The product is easily isolated from the reaction mixture when using this procedure. This procedure will also work with other ketone protecting groups. In addition, the corresponding ketoacid can be used as a precursor to the α-ketoamide via coupling with an amine $RNH_2$ using standard peptide coupling reagents would result in formation of the peptide α-ketoamide.

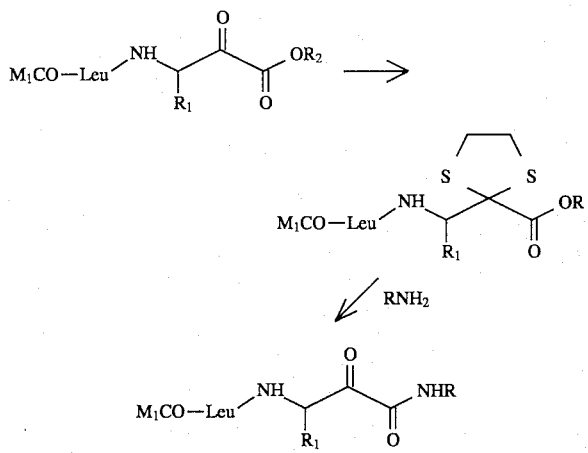

The techniques for synthesis of a wide variety of amines are described in many publications. For example, Evans et al. [*J. Org. Chem.* 39, 914 (1974); incorporated herein by reference] reported the syntheses of phenylethanol derivatives with alkylamino, alkoxyamino and phenyloxyamino groups. Katrizky et al. [*J. Chem. Soc.* 2404–2408 (1956); incorporated herein by reference], Fife et al. [*Heterocycles,* 22(1), 93–96 (1984), *Heterocycles,* 22(5), 1121–1124 (1984); incorporated herein by reference], and Isoda et al. [*Chemical and Pharmaceutical Bulletin,* 28, 1408–14 14(1980); incorporated herein by reference] reported the syntheses of pyridine derivatives with alkylamino and COOR groups. Nagata et al. [*Yakugaku Zasshi,* 83,679–682 (1963); incorporated herein by reference] reported the syntheses of quinoline derivatives with alkylamino groups. Zimmer et al. [*Tetrahedron Letters,* 24, 2805–2807 (1968); incorporated herein by reference]reported the syntheses of isoquinoline derivatives with alkylamino groups. Aroyan et al. [*Izv. Akad. Nauk Arm. SSR, KMm. Nauki,* 18(1), 76–82 (1965); incorporated herein by reference] reported the syntheses of tetrahydroquinoline derivatives with alkylamino groups. Yonan, [U.S. Pat. No. 3,245,997(Cl. 260–288), Apr. 12, 1966.2 pp; incorporated herein by reference] reported the syntheses of tetrahydroisoquinoline derivatives with alkylamino groups. Rybar et al. [Chem. Commun. 35, 1415–1433 (1970); incorporated herein by reference], Golovchinskaya et al. [*J. General Chem.* 22, 599–603 (1952); incorporated herein by reference], and Nantka-Namirski et sl. [Acta. Polon. Pharm. 1, 5–12 (1974); incorporated herein by reference] reported the syntheses of caffeine derivatives with alkylamino groups. Goldberg et al. [*J. Chem. Soc.* 1372 (1947); incorporated herein by reference] reported the syntheses of methylthiazole derivatives with alkylamino groups. Mizuno et al. [*J. Org. Chem.* 39, 1250 (1974); incorporated herein by reference] reported the syntheses of pyridine-N-oxide derivatives with alkylamino groups. Wade [*J. Heterocyclic Chem.* 23, 981 (1986)] reported the syntheses of uracil derivatives with alkylamino groups.

EXAMPLES

The follow detailed examples are given to illustrate the invention and are not intended to limit it in any manner.

Example 1

Z-Leu-Abu-CONH—$(CH_2)_5$OH.

This compound was synthesized from 1,3-dithiolane derivative of Z-Leu-Abu-COOEt and 5-amino-1-pentanol. To a solution of protected α-ketoester (1 mmol) in ethanol (3 mL) was added 5-amino-1-pentanol (3 mmol) and stirred overnight at r.t. To the mixture was added AcOEt (25 mL) and white precipitate was filtered. The filtrate was washed with cold 1N HCl (2×10 mL), water (1×10 mL), saturated NaCl (2×10 mL) and dried over $MgSO_4$. After evaporation of the solvent, chromatography on a silica gel column using $CHCl_3/CH_3OH$ 10:1 followed by precipitation from AcOEt/hexane afforded a white solid (42% yield). Single spot on TLC, $R_f$=0.54 ($CHCl_3/CH_3OH$ 10:1), mp 122°–123° C. $^1$H NMR ($CDCl_3$) ok, MS (FAB) m/e=464 (M+1). Anal: calcd. for $C_{24}H_{37}N_3O_6$, 463; C, 62.18; H, 8.04; N, 9.06. Found: C, 61.52; H, 7.96; N, 8.98.

Example 2

Z-Leu-Abu-CONH—$(CH_2)_2$OH.
This compound was synthesized from 1,3-dithiolane derivative of Z-Leu-Abu-COOEt and ethanolamine by the procedure described in Example 1, and purified by column chromatography using $CHCl_3/CH_3OH$ 10:1 (40% yield). White solid, single spot on TLC, $R_f$=0.42 ($CHCl_3/CH_3OH$ 10:1), mp 151°– 154° C. $^1$H NMR ($CDCl_3$) ok, MS (FAB) m/e=422 (M+1). Anal: calcd. for $C_{21}H_{31}N_3O_6$, 421; C, 59.84; H, 7.41; N, 9.97. Found: C, 59.11; H, 7.44; N, 9.81.

Example 3

Z-Leu-Abu-CONH—$(CH_2)_2O(CH_2)_2$OH.
This compound was synthesized from 1,3-dithiolane derivative of Z-Leu-Abu-COOEt and 2-(2-aminoethoxy) ethanol by the procedure described in Example 1, and purified by column chromatography using $CHCl_3/CH_3OH$ 10:1 (34% yield). White solid, single spot on TLC, $R_f$=0.42 ($CHCl_3/CH_3OH$ 10:1),mp 103°–105° C. $^1$H NMR ($CDCl_3$) ok, MS (FAB) m/e=466 (M+1). Anal: calcd. for $C_{23}H_{35}N_3O_7$, 465; C, 59.30; H, 7.58; N, 9.02. Found: C, 59.23; H, 7.58; N, 9.01.

Example 4

Z-Leu-Abu-CONH—$CH_2CH(OCH_3)_2$.
This compound was synthesized from 1,3-dithiolane derivative of Z-Leu-Abu-COOEt and aminoacetaldehyde dimethylacetal by the procedure described in Example 1, and purified by column chromatography using $CHCl_3/CH_3OH$ 20:1 (25% yield). White solid., single spot on TLC, $R_f$=0.47 ($CHCl_3/CH_3OH$ 20: 1), mp 99°–102° C. $^1$H NMR ($CDC_{13}$) ok, MS (FAB) m/e=466 (M+1). Anal: calcd. for $C_{23}H_{35}N_3O_7$, 465; C, 59.30; H, 7.58; N, 9.02. Found: C, 58.95; H, 7.71; N, 9.00.

Example 5

Z-Leu-Abu-CONH—$CH_2CH(OC_2H_5)_2$.
This compound was synthesized from 1,3-dithiolane derivative of Z-Leu-Abu-COOEt and aminoacetaldehyde diethylacetal, and purified by column chromatography using $CHCl_3/CH_3OH$ 20:1 (36% yield). White solid, single spot on TLC, $R_f$=0.37 ($CHCl_3/CH_3OH$ 20: 1), mp 100°–103° C. $^1$H NMR ($CDCl_3$) ok, MS (FAB) m/e=494 (12%, M+1), 448 (100%, M+1–45). Anal: calcd. for $C_{25}H_{39}N_3O_7$, 493; C, 60.83; H, 7.96; N, 8.51. Found: C, 60.73; H, 7.98; N, 8.42.

Example 6

Z-Leu-Abu-CONH—$CH_2$—$C_6H_8(1,3,3-(CH_3)_3$-5-OH).
This compound was synthesized from 1,3-dithiolane derivative of Z-Leu-Abu-COOEt and 3-aminomethyl-3,5,5,-trimethyl-cyclohexanol, and purified by column chromatography using $CHCl_3/CH_3OH$ 30:1 (51% yield). White solid, single spot on TLC, $R_f$=0.55 ($CHCl_3/CH_3OH_{30:1}$), mp 59°–61° C. $^1$H NMR($CDCl_3$) ok, MS (FAB) m/e=532 (M+1). Anal; calcd. for $C_{29}H_{45}N_3O_6$,531; C, 65.51; H, 8.53; N, 7.90. Found, C, 65.21; H, 8.55, N, 7.81.

Example 7

Z-Leu-Abu-CONH—$(CH_2)_2C_6H_4$(4-OH).
This compound was synthesized from 1,3-dithiolane derivative of Z-Leu-Abu-COOEt and 4-(2-aminoethyl)phenol, and purified by column chromatography using $CHCl_3/CH_3OH$ 30:1 (60% yield). White solid, single spot on TLC, Rf=0.56 ($CHCl_3/CH_3OH$ 30:1), mp 151°–153° C. $^1$H NMR ($CDCl_3$) ok, MS (FAB) m/e=498 (M+1). Anal: calcd. for $C_{27}H_{35}N_3O_6$, 497; C, 65.17; H, 7.09; N, 8.45. Found, C, 65.16; H, 7.13, N, 8.52.

Example 8

Z-Leu-Abu-CONH—(CH$_2$)$_2$C$_6$H$_4$(2-OCH$_3$).

This compound was synthesized from 1,3-dithiolane derivative of Z-Leu-Abu-COOEt and 2-methoxyphenethylamine, and purified by column chromatography using CHCl$_3$/CH$_3$OH 50:1), (71% yield). Yellow solid, single spot on TLC, R$_f$=0.47 (CHCl$_3$/CH$_3$OH 50:1 ), mp 101°–103° C. $^1$H NMR(CDCl$_3$) ok, MS (FAB) m/e=512(M+1). Anal; calcd. for C$_{28}$H$_{37}$N$_3$O$_6$, 511; C, 65.73; H, 7.29; N, 8.21. Found, C, 65.50; H, 7.31; N, 8.19.

Example 9

Z-Leu-Abu-CONH—(CH$_2$)$_2$C$_6$H$_4$(3-OCH$_3$).

This compound was synthesized from 1,3-dithiolane derivative of Z-Leu-Abu-COOEt and 3-methoxyphenethylamine, and purified by column chromatography using CHCl$_3$/CH$_3$OH 50:1 (56% yield). Yellow solid, single spot on TLC, R$_f$=0.46 (CHCl$_3$/CH$_3$OH 50:1 ), mp 99°–100° C. $^1$H NMR (CDCl$_3$) ok, MS (FAB) m/e=512 (M+1). Anal: calcd. for C$_{28}$H$_{37}$N$_3$O$_6$, 511; C, 65.73; H, 7.29; N, 8.21. Found, C, 65.62; H, 7.34; N, 8.16.

Example 10

Z-Leu-Abu-CONH—(CH$_2$)$_2$C$_6$H$_4$(4-OCH$_3$).

This compound was synthesized from 1,3-dithiolane derivative of Z-Leu-Abu-COOEt and 4-methoxyphenethylamine, and purified by column chromatography using CHCl$_3$/CH$_3$OH 50:1 (50% yield). White solid, single spot on TLC, R$_f$=0.46 (CHCl$_3$/CH$_3$OH 50:1 ), mp 152°–155° C. $^1$H NMR(CDCl$_3$) ok, MS(FAB) m/e=512(M+1). Anal:calcd. for C$_{28}$H$_{37}$N$_3$O$_6$, 511; C, 65.73; H, 7.29; N, 8.21. Found, C, 65.64; H, 7.30; N, 8.19.

Example 11

Z-Leu-Abu-CONH—CH$_2$C$_6$H$_3$(3,5-(OCH$_3$)$_2$.

This compound was synthesized from 1,3-dithiolane derivative of Z-Leu-Abu-COOEt and 3,5-dimethoxyphenethylamine, and purified by column chromatography using CHCl$_3$/CH$_3$OH 50:1 (50% yield). White solid, single spot on TLC, R$_f$=0.46 (CHCl$_3$/CH$_3$OH 50:1 ), mp 153°–155° C. $^1$H NMR (CDCl$_3$) ok, MS (FAB) m/e=528 (M+1). Anal: calcd. for C$_{28}$H$_{37}$N$_3$O$_7$, 527; C, 63.74; H, 7.07; N, 7.96. Found, C, 63.66; H, 7.09; N, 7.92.

Example 12

Z-Leu-Abu-CONH—CH$_2$CH(OH)Ph.

This compound was synthesized from 1,3-dithiolane derivative of Z-Leu-Abu-COOEt and 2-amino-1-phenylethanol by the procedure described in Example 1, and purified by column chromatography using CHCl$_3$/CH$_3$OH 10:1 (50% yield). White solid, single spot on TLC, R$_f$=0.48 (CHCl$_3$/CH$_3$OH 10:1), mp 152°–154° C. $^1$H NMR (CDCl$_3$) ok, MS (FAB) m/e=498 (M+1). Anal: calcd. for C$_{27}$H$_{35}$N$_3$O$_6$, 497; C, 65.17; H, 7.09; N, 8.44. Found, C, 65.06; H, 7.05; N, 8.50.

Example 13

Z-Leu-Abu-CONH—CH$_2$CH(OH)C$_6$H$_4$(4-OCH$_3$).

This compound was synthesized using 2-amino-1(4-methoxy)phenylethanol and purified by column chromatography using AcOEt/hexane 3:2 (26% yield). Yellow solid, single spot on TLC, R$_f$=0.56 (AcOEt/hexane 1:1 ),mp 128°–129° C. $^1$H NMR (CDCl$_3$) ok, MS (FAB) m/e=528 (M+1). Anal: calcd. for C$_{28}$H$_{37}$N$_3$O$_{7, 527}$; C, 63.74; H, 7.07; N, 7.96. Found, C, 63.44; H, 7.08; N, 7.82.

Example 14

Z-Leu-Abu-CONH—CH$_2$CH(OH)C$_6$H$_2$(2,4,6-(OCH$_3$)$_3$).

This compound was synthesized using 2-amino-1(2,4,6-trimethoxy)phenylethanol and purified by column chromatography using CHCl$_3$/CH$_3$OH 20:1 followed by CHCl$_3$/CH$_3$OH 10:1 (29% yield). Yellow solid, single spot on TLC, R$_f$=0.54 (CHCl$_3$/CH$_3$OH 10:1), mp 170°–172° C. $^1$H NMR (CDCl$_3$) ok, MS (FAB) m/e=588 (90%, M+1), 570 (100%, M+1). Anal: calcd. for C$_{30}$H$_{41}$N$_3$O$_9$, 587; C, 61.31; H, 7.03; N, 7.15. Found, C, 60.86; H, 7.29; N, 6.95.

Example 15

Z-Leu-Abu-CONH—CH$_2$CH(OH)C$_6$H$_4$(4-N(CH$_3$)$_2$).

This compound was synthesized using 2-amino-1(4-dimethylamino)phenylethanol and purified by column chromatography using AcOEt/hexane 6:1 (23% yield). Yellow solid, single spot on TLC, R$_f$=0.41 (AcOEt/hexane 6:1), mp 104° C. (dec.). $^1$H NMR (CDCl$_3$) ok, MS (FAB) m/e=523 (M+1-18). Anal: calca. for C$_{29}$H$_{40}$N$_4$O$_6$, 540; C, 64.42; H, 7.45; N, 10.36. Found, C, 64.27, H, 7.42; N, 10.34.

Example 16

Z-Leu-Abu-CONH—CH$_2$CH(OH)C$_6$F$_5$.

This compound was synthesized using 2-amino-1-pentafluorophenylethanol and purified by column chromatography using CHCl$_3$/CH$_3$OH 10:1 (66% yield). White solid, single spot on TLC, R$_f$=0.28 (CHCl$_3$/CH$_3$OH 10:1), mp 167°–171° C. $^1$H NMR (DMSO-d$_6$) ok, MS (FAB) m/e=570 (M+1-18). Anal: calcd. for C$_{27}$H$_{30}$N$_3$O$_6$F$_5$, 587; C, 55.19; H, 5.14; N, 7.15. Found, C, 56.13; H, 5.58; N, 7.20.

Example 17

Z-Leu-Abu-CONH—CH$_2$CH(OH)C$_6$H$_4$(3-CF$_3$).

This compound was synthesized using 2-amino-1(3-trifluoromethyl)phenylethanol and purified by column chromatography using CHCl$_3$/CH$_3$OH 10:1 (72% yield). Dark yellow semisolid, single spot on TLC, R$_f$=0.48 (CHCl$_3$/CH$_3$OH 10:1). $^1$H NMR (CDCl$_3$) ok, MS (FAB) m/e=566 (M+1). Anal: calcd. for C$_{28}$H$_{34}$N$_3$O$_6$F$_3$, 565; C, 59.46; H, 6.06; N, 7.42. Found, C, 59.12; H, 6.18; N, 7.14.

Example 18

Z-Leu-Abu-CONH—CH$_2$CH(OH)C$_6$H$_4$(3-OPh).

This compound was synthesized using 2-amino-1(3-phenoxy)phenylethanol and purified by column chromatography using CHCl$_3$/CH$_3$OH 10:1 (67% yield). Yellow oil, single spot on TLC, R$_f$=0.54 (CHCl$_3$/CH$_3$OH 10:1). $^1$H NMR (CDCl$_3$) ok, MS (FAB) m/e=590 (53%, M+1), 572 (100%, M+1-18). Anal: Calcd. for C$_{33}$H$_{39}$N$_3$O$_7$, 589; C, 67.21; H, 6.66; N, 7.12. Found, C, 66.76; H, 6.25; N, 7.06.

Example 19

Z-Leu-Abu-CONH—CH$_2$CH(OH)C$_6$H$_4$(4-OPh).

This compound was synthesized using 2-amino-1(4-phenoxy)phenylethanol and purified by column chromatography using CHCl$_3$/CH$_3$OH 20:1 (48% yield). Yellow semisolid, single spot on TLC, R$_f$=0.22 (CHCl$_3$/CH$_3$OH 20:1), mp 55°–60° C. $^1$H NMR (CDCl$_3$) ok, MS (FAB) m/e=590 (47%, M+1),572 (100%, M+1-18). Anal: calcd. for $C_{33}H_{39}N_3O_7$, 589; C, 67.21; H, 6.66; N, 7.12. Found, C, 67.30; H, 6.67; N, 7.10.

Example 20

Z-Leu-Abu-CONH—$CH_2CH(OH)C_6H_4$(4-$OCH_2Ph$).

This compound was synthesized using 2-amino-1 (4-benzyloxy)phenylethanol and purified by column chromatography using $CHCl_3/CH_3OH$ 20:1 (39% yield). Yellow solid, single spot on TLC, $R_f$=0.40 ($CHCl_3/CH_3OH$ 20:1), mp 59°–62° C. $^1H$ NMR ($CDCl_3$) ok, MS (FAB) m/e=604 (M+1). Anal: calcd. for $C_{34}H_{41}N_3O_7$, 603; C, 67.64; H, 6.84; N, 6.96. Found, C, 67.50; H, 6.87; N, 6.90.

Example 21

Z-Leu-Abu-CONH—$CH_2CH(OH)C_6H_4$-3-$OC_6H_4$(3-$CF_3$).

This compound was synthesized using 2-amino-1(3-(3'-trifluoromethyl)phenoxy)phenylethanol and purified by column chromatography using $CHCl_3/CH_3OH$ 30:1 (57% yield). Yellow solid, single spot on TLC, $R_f$=0.40 ($CHCl_3/CH_3OH$ 30:1 ), mp 97°–101° C. $^1H$ NMR ($CDCl_3$) ok, MS (FAB) m/e=658 (M+1). Anal: calcd. for $C_{34}H_{38}N_3O_7F_3$, 657; C, 62.09; H, 5.82; N, 6.39. Found, C, 62.05; H, 5.84; N, 6.42.

Example 22

Z-Leu-Abu-CONH—$CH_2CH(OH)C_6H_4$-3-$OC_6H_3$(3,4-$Cl_2$).

This compound was synthesized using 2-amino-1(3-(3',4'-dichloro)phenoxy)phenylethanol and purified by column chromatography using $CHCl_3/CH_3OH$ 20:1 (55% yield). Yellow solid, single spot on TLC, $R_f$=0.28 ($CHCl_3/CH_3OH$ 20: 1), mp 63°–67° C. $^1H$ NMR ($CDCl_3$) ok, MS (FAB) m/e=659 (M+1). Anal: calcd. for $C_{33}H_{37}N_3O_7Cl_2$, 658; C, 60.18; H, 5.66; N, 6.38. Found, C, 59.37; H, 5.12; N, 6.16.

Example 23

Z-Leu-Abu-CONH—$CH_2CH(OH)C_6H_3$(3,4-($OCH_2Ph$)$_2$).

This compound was synthesized using 2-amino-1(3,4-dibenzyloxy)phenylethanol and purified by column chromatography using $CHCl_3/CH_3OH$ 10:1 (60% yield). White solid, single spot on TLC, $R_f$=0.48 ($CHCl_3/CH_3OH$ 10:1), mp 101°–104° C. $^1H$ NMR ($CDCl_3$) ok, MS(FAB) m/e= 710(M+1). Anal:calcd. for $C_{41}H_{47}N_3O_8$, 709;C, 69.37;H, 6.67;N, 5.92. Found, C, 68.23; H, 6.70; N, 6.08.

Example 24

Z-Leu-Abu-CONH—$CH_2CH(OH)$-1-$C_{10}H_7$.

This compound was synthesized using 2-amino-1(1-naphthyl)phenylethanol and purified by column chromatography using AcOEt/hexane 1:1 (15% yield). Pale orange solid, single spot on TLC, $R_f$=0.48 (AcOEt/hexane 1:1 ), mp 63°–71° C. $^1H$ NMR ($CDCl_3$) ok, MS (FAB) m/e=548 (M+1). Anal: calcd. for $C_{31}H_{37}N_3O_6$, 547; C, 67.99; H, 6.81; N, 7.67. Found, C, 67.73; H, 7.03; N, 7.40.

Example 25

Z-Leu-Abu-CONH—$CH_2CH(OH)$-2-$C_{10}H_7$.

This compound was synthesized using 2-amino-1(2-naphthyl)phenylethanol and purified by column chromatography using AcOEt/hexane 3:2 (17% yield). Orange solid, single spot on TLC, $R_f$=0.39 (AcOEt/hexane 3:1), mp 137°–140° C. $^1H$ NMR ($CDCl_3$) ok, MS (FAB) m/e=548 (M+1). Anal: calcd. for $C_{31}H_{37}N_3O_6$, 547; C, 67.99; H, 6.81; N, 7.67. Found, C, 68.15; H, 6.83; N, 7.43.

Example 26

Z-Leu-Phe-CONH—$CH_2CH(OH)Ph$.

This compound was synthesized using 2-amino-1-phenylethanol and purified by column chromatography using $CHCl_3/CH_3OH$ 10:1 (46% yield). White solid, single spot on TLC, $R_f$=0.72 ($CHCl_3/CH_3OH$ 10:1), mp 164°–166° C. $^1H$ NMR ($CDCl_3$) ok, MS (FAB) m/e=560 (M+1). Anal: calcd. for $C_{32}H_{37}N_3O_6$, 559; C,68.67; H, 6.66; N, 7.51. Found, C, 68.46, H, 6.68, N, 7.50.

Example 27

Z-Leu-Phe-CONH—$CH_2CH(OH)C_6H_4$(4-$N(CH_3)_2$).

This compound was prepared using 2-amino-1(4-dimethylamino)phenylethanol and purified by column chromatography using $CHCl_3/CH_3OH$ 10:1 (22% yield). Yellow solid, single spot on TLC, $R_f$=0.68 ($CHCl_3/CH_3OH$ 10:1), mp 130° C. (dec.). $^1H$ NMR ($CDCl_3$) ok, MS (FAB) m/e=603 (35%, M+1), 585 (100%, M+1-18). Anal: calcd. for $C_{34}H_{42}N_4O_6$, 602; C, 67.75, H, 7.02, N, 9.29. Found, C, 66.43; H, 7.06; N, 9.22.

Example 28

Z-Leu-Phe-CONH—$CH_2CH(OH)C_6F_5$.

This compound was prepared using 2-amino-1-pentafluorophenylethanol and purified by column chromatography using $CHCl_3/CH_3OH$ 20:1 (47% yield). White solid, single spot on TLC, $R_f$=0.45 ($CHCl_3/CH_3OH$ 20:1), mp 191°–192° C. $^1H$ NMR (DMSO-$d_6$) ok, MS (FAB) m/e=632 (100%, M+1-18). Anal: calcd. for $C_{32}H_{32}N_3O_6F_5$, 649; C, 59.16; H, 4.96; N, 6.46. Found, C, 61.18; H, 5.37; N, 6.68.

Example 29

Z-Leu-Phe-CONH—$CH_2CH(OH)C_6H_4$(3-$CF_3$).

This compound was prepared using 2-amino-1(3-trifluoromethyl)phenylethanol and purified by column chromatography using $CHCl_3/CH_3OH$ 20:1 (42% yield). Dark yellow semisolid, single spot on TLC, $R_f$=0.48 ($CHCl_3/CH_3OH$ 10:1). $^1H$ NMR ($CDCl_3$) ok, MS (FAB) m/e=628 (M+1). Anal: calcd. for $C_{33}H_{36}N_3O_6F_3$, 627; C, 63.15; H, 5.78; N, 6.69. Found, C, 63.24; H, 5.82; N, 6.65.

Example 30

Z-Leu-Phe-CONH—$CH_2CH(OH)C_6H_4$(3-OPh).

This compound was prepared using 2-amino-1 (3-phenoxy)phenylethanol and purified by column chromatography using $CHCl_3/CH_3OH$ 20:1 (50% yield). Yellow semisolid, single spot on TLC, $R_f$=0.25 ($CHCl_3/CH_3OH$ 20:1). $^1H$ NMR ($CDCl_3$) ok, MS (FAB) m/e=652 (M+1). Anal: Calcd. for $C_{38}H_{41}N_3O_7$, 651; C, 70.02; H, 6.34; N, 6.44. Found, C, 69.67; H, 6.60; N, 6.23.

Example 31

Z-Leu-Phe-CONH—$CH_2CH(OH)C_6H_4$(4-OPh).

This compound was prepared using 2-amino-1(4-phenoxy)phenylethanol and purified by column chromatography using $CHCl_3/CH_3OH$ 30:1 (30% yield). Yellow semisolid, single spot on TLC, $R_f$=0.20 ($CHCl_3/CH_3OH$ 30: 1), mp 146°–149° C. $^1H$ NMR ($CDCl_3$) ok, MS (FAB) m/e=652 (25%, M+1), 634 (100%,M+1-18). Anal: calcd. for $C_{38}H_{41}N_3O_7$, 651; C, 70.02; H, 6.34; N, 6.44. Found, C, 70.14; H, 6.36; N, 6.38.

Example 32

Z-Leu-Phe-CONH—CH$_2$CH(OH)C$_6$H$_4$(4-OCH$_2$Ph).

This compound was prepared using 2-amino-1(4-benzyloxy)phenylethanol and purified by column chromatography using CHCl$_3$/CH$_3$OH 20:1 (49% yield). Yellow solid, single spot on TLC, R$_f$=0.45 (CHCl$_3$/CH$_3$OH 20:1), mp 133°–134° C. $^1$H NMR (CDCl$_3$) ok, MS (FAB) me=666 (M+1). Anal: calcd. for C$_{39}$H$_{43}$N$_3$O$_7$, 665; C, 70.35; H, 6.51; N, 6.31. Found, C, 69.55; H, 6.46; N, 6.25.

Example 33

Z-Leu-Phe-CONH—CH$_2$CH(OH)C$_6$H$_4$-3-OC$_6$H$_4$(3-CF$_3$).

This compound was prepared using 2-amino-1(3-trifluoromethyl)phenoxy)phenylethanol and purified by column chromatography using CHCl$_3$/CH$_3$OH 20:1 (52% yield). Yellow solid, single spot on TLC, R$_f$=0.23 (CHCl$_3$/CH$_3$OH 20:1), mp 142°–143° C. $^1$H NMR (CDCl$_3$) ok, MS (FAB) m/e=720 (M+1). Anal: calcd. for C$_{39}$H$_{40}$N$_3$O$_7$F$_3$, 719; C, 65.08; H, 5.60; N, 5.72. Found, C, 64.66; H, 5.58; N, 5.72.

EXample 34

Z-Leu-Phe-CONH—CH$_2$CH(OH)C$_6$H$_4$-3-OC$_6$H$_3$(3,4-Cl$_2$).

This compound was prepared using 2-amino-1(3-(3',4'-dichloro)phenoxy)phenylethanol and purified by column chromatography using CHCl$_3$/CH$_3$OH 20:1 (41% yield). Yellow solid, single spot on TLC, R$_f$=0.40 (CHCl$_3$/CH$_3$OH 20: 1), mp 136°–137° C. $^1$H NMR (CDCl$_3$) ok, MS (FAB) m/e=721 (M+1). Anal: calcd. for C$_{38}$H$_{39}$N$_3$O$_7$Cl$_2$, 720; C, 63.33; H, 5.45; N, 5.83. Found, C, 62.78; H, 5.09; N, 5.42.

Example 35

Z-Leu-Phe-CONH—CH$_2$CH(OH)C$_6$H$_3$(3,4-(OCH$_2$Ph)2).

This compound was prepared using 2-amino-1(3,4-dibenzyloxy)phenylethanol and purified by column chromatography using CHCl$_3$/CH$_3$OH 20:1 (45% yield). Yellow solid, single spot on TLC, R$_f$=0.42(CHCl$_3$/CH$_3$OH20:1),mp 149°–152° C. $^1$H NMR(CDCl$_3$) ok, MS (FAB) m/e=772 (M+1). Anal: calcd. for C$_{46}$H$_{49}$N$_3$O$_8$, 771; C, 71.57; H, 6.39; N, 5.44. Found, C, 71.33; H, 6.45; N, 5.41.

Example 36

Z-Leu-Abu-CONH—CH$_2$-2-Furyl.

This compound was synthesized from 1,3-dithiolane derivative of Z-Leu-Abu-COOEt and 2-furfurylamine by the procedure described in Example 1, and purified by column chromatography using CHCl$_3$/CH$_3$OH 20:1 (43% yield). White solid, single spot on TLC, R$_f$=0.68 (CHCl$_3$/CH$_3$OH 10:1), mp 138°–139° C. $^1$H NMR (CDCl$_3$) ok, MS (FAB) m/e=458 (M+1). Anal: calcd. for C$_{24}$H$_{31}$N$_3$O$_6$, 457; C, 63.00; H, 6.83; N, 9.18. Found, C, 62.22; H, 6.72; N, 9.00.

Example 37

Z-Leu-Abu-CONH—CH$_2$-2-Tetrahydrofuryl.

This compound was synthesized using 2-tetrahydrofurfurylamine and purified by column chromatography using CHCl$_3$/CH$_3$OH 20:1 (35% yield). Yellow solid, single spot on TLC, R$_f$=0.59 (CHCl$_3$/CH$_3$OH 20: 1), mp 126°–128° C. $^1$H NMR (CDCl$_3$) ok, MS (FAB) m/e=462 (M+1). Anal: calcd. for C$_{24}$H$_{35}$N$_3$O$_6$, 461; C, 62.45; H, 7.64; N, 9.10. Found, C, 62.37; H, 7.63; N, 9.19.

Example 38

Z-Leu-Abu-CONH—CH$_2$-2-Pyridyl.

This compound was synthesized from 1,3-dithiolane derivative of Z-Leu-Abu-COOEt and 2-aminomethylpyridine. After reacting overnight at r.t., to the mixture was added AcOEt (25 mL) and white precipitate was filtered. The filtrate was washed with water (3×10 mL), saturated NaCl (2×10 mL) and dried over MgSO$_4$. After evaporation of the solvent, chromatography on a silica gel column using CHCl$_3$/CH$_3$OH 10:1 followed by precipitation from AcOEt/hexane afforded a yellow solid (50% yield).

Single spot on TLC, R$_f$=0.50 (CHCl$_3$/CH$_3$OH 10: 1), mp 117°–119° C. $^1$H NMR (CDCl$_3$) ok, MS (FAB) m/e=469 (M+1). Anal: calcd. for C$_{25}$H$_{32}$N$_4$O$_5$, 468; C, 64.08; H, 6.88; N, 11.96. Found, C, 63.93; H, 6.86; N, 11.85.

Example 39

Z-Leu-Abu-CONH—CH$_2$-3-Pyridyl.

This compound was synthesized from 1,3-dithiolane derivative of Z-Leu-Abu-COOEt and 3-aminomethylpyridine by the procedure described in Example 38, and purified by column chromatography using CHCl$_3$/CH$_3$OH 10:1 (35% yield). Yellow solid, single spot on TLC, R$_f$=0.54 (CHCl$_3$/CH$_3$OH 10:1), mp 122°–123° C. $^1$H NMR (CDCl$_3$) ok, MS (FAB) m/e=469 (M+1). Anal: calcd. for C$_{25}$H$_{32}$N$_4$O$_5$, 468; C, 64.08; H, 6.88; N, 11.96. Found, C, 63.98; H, 6.91; N, 11.97.

Example 40

Z-Leu-Abu-CONH—CH$_2$-4-Pyridyl.

This compound was synthesized using 4-aminomethylpyridine and purified by column chromatography using CHCl$_3$/CH$_3$OH 10:1 (45% yield). Yellow solid, single spot on TLC, R$_f$=0.55(CHCl$_3$/CH$_3$OH 10:1), mp 124°–126° C. $^1$H NMR (CDCl$_3$) ok, MS (FAB) m/e=469 (M+1). Anal: calcd. for C$_{25}$H$_{32}$N$_4$O$_5$, 468; C, 64.08; H, 6.88; N, 11.96. Found, C, 63.88; H, 6.87; N, 11.96.

Example 41

Z-Leu-Abu-CONH—(CH$_2$)$_2$-2-Pyridyl.

This compound was synthesized using 2-(2-aminoethyl)pyridine and purified by column chromatography using CHCl$_3$/CH$_3$OH 10:1 (53% yield). Yellow solid, single spot on TLC, R$_f$=0.60 (CHCl$_3$/CH$_3$OH 10:1), mp 128°–130° C. $^1$H NMR (CDCl$_3$) ok, MS (FAB) m/e=483 (M+1). Anal: calcd. for C$_{26}$H$_{34}$N$_4$O$_5$, 482; C, 64.71; H, 7.10; N, 11.61. Found, C, 64.04; H, 7.05; N, 11.49.

Example 42

Z-Leu-Abu-CONH—(CH$_2$)2-2-(N-Methylpyrrole).

This compound was synthesized from protected Z-Leu-Abu-COOEt and 2(2-aminoethyl)-1-methylpyrrole by the procedure described in Example 38, and purified by column chromatography using CHCl$_3$/CH$_3$OH 30:1 (16% yield). Orange semisolid, single spot on TLC, R$_f$=0.34 (CHCl$_3$/CH$_3$OH 30:1), mp 1.20°–123° C. 1H NMR (CDCl$_3$) ok, MS (FAB) m/e=485 (M+1). Anal: calcd. for C$_{26}$H$_{36}$N$_4$O$_5$, 484; C, 64.44; H, 7.48; N, 11.56. Found, C, 64.02; H, 7.26; N, 11.21.

Example 43

Z-Leu-Abu-CONH—(CH$_2$)$_3$-1-Imidazolyl.

This compound was synthesized using 1(3-aminopropyl)imidazole by the procedure described in Example 38, and purified by column chromatography using CHCl$_3$/CH$_3$OH 10:1 (27% yield). Yellow semisolid, single spot on TLC, $R_f$=0.33 (CHCl$_3$/CH$_3$OH 10:1), mp 52°–55° C. $^1$H NMR (CDCl$_3$) ok, MS (FAB) m/e=486 (M+1). Anal: calcd. for C$_{25}$H$_{35}$N$_5$O$_5$, 485; C, 61.83; H, 7.26; N, 14.42. Found, C, 60.90; H, 7.21; N, 13.87.

Example 44

Z-Leu-Abu-CONH—(CH$_2$)$_2$-4-Morpholinyl.

This compound was synthesized using 4-(2-aminoethyl)morpholine and purified by column chromatography using CHCl$_3$/CH$_3$OH 10:1 (55% yield). Yellow semisolid, single spot on TLC, $R_f$=0.49 (CHCl$_3$/CH$_3$OH 10:1), mp 124°–126° C. $^1$H NMR(CDCl$_3$) ok, MS (FAB) m/e=491 (M+1). Anal: calcd. for C$_{25}$H$_{38}$N$_4$O$_6$, 490; C, 61.15; H, 7.81; N, 11.42. Found, C, 61,08; H, 7.86; N, 11.34.

Example 45

Z-Leu-Abu-CONH—(CH$_2$)$_3$-4-Morpholinyl.

This compound was synthesized using 4-(3-aminopropyl)morpholine and purified by column chromatography using CHCl$_3$/CH$_3$OH 10:1 (42% yield). Yellow semisolid, single spot on TLC, $R_f$=0.50 (CHCl$_3$/CH$_3$OH 10:1), mp 125°–126° C. $^1$H NMR (CDCl$_3$) ok, MS (FAB) m/e=505 (M+1). Anal: calcd. for C$_{26}$H$_{40}$N$_4$O$_6$, 504; C, 61.88; H, 7.99; N, 11.10. Found, C, 61,69; H, 7.95; N, 11.07.

Example 46

Z-Leu-Abu-CONH—(CH$_2$)$_3$-1-Pyrrolidinyl-2-one.

This compound was prepared from Z-Leu-Abu-COOH and 1-(3-aminopropyl)2-pyrrolidinone, and purified by column chromatography using CHCl$_3$/CH$_3$OH 10:1 (33% yield). White semisolid, single spot on TLC, $R_f$=0.51 (CHCl$_3$/CH$_3$OH 10:1). $^1$H NMR (CDCl$_3$) ok, MS (FAB), m/e=503 (M+1). Anal: calcd. for C$_{26}$H$_{38}$N$_4$O$_6$, 502; C, 62.13; H, 7.62; N, 11.14. Found, C, 62.02; H, 7.71; N, 10.52.

Example 47

Z-Leu-Abu-CONH—(CH$_2$)$_2$-3-Indolyl.

This compound was prepared from Z-Leu-Abu-COOH and 3-(2-aminoethyl)indole and purified by column chromatography using CHCl$_3$/CH$_3$OH 30:1 (18% yield). White semisolid, single spot on TLC, $R_f$=0.47 (CHCl$_3$/CH$_3$OH 30:1). $^1$H NMR (CDCl$_3$) ok, MS (exact FAB), m/e=521 2745.

Example 48

Z-Leu-Abu-CONH—CH$_2$-2-Quinolinyl.

This compound was prepared from 1,3-dithiolane derivative of Z-Leu-Abu-COOEt and 2-aminomethylquinoline by the procedure described in Example 38, and purified by column chromatography using AcOEt/hexane 2:1 (16% yield). Yellow solid, single spot on TLC, $R_f$=0.27 (AcOEt/hexane 2:1), mp 135°–138° C. $^1$H NMR (CDCl$_3$) ok, MS (FAB) m/e=519 (M+1). Anal: calcd. for C$_{29}$H$_{34}$N$_4$O$_5$, 518; C, 67.16; H, 6.60; N, 10.80. Found, C, 66.89; H, 6.68; N, 10.61.

Example 49

Z-Leu-Abu-CONH—CH$_2$-1-Isoquinolinyl.

This compound was prepared using 1-aminomethylisoquinoline and purified by column chromatography using AcOEt/hexane 2:1 (12% yield). Yellow solid, single spot on TLC, $R_f$=0.34 (AcOEt/hexane1:1), mp 121°–125° C. $^1$H NMR (CDCl$_3$) ok, MS (FAB)m/e=519(M+1). Anal: calcd. for C$_{29}$H$_{34}$N$_4$O$_5$, 518; C, 67.16; H, 6.60; N, 10.80. Found, C, 67.11; H, 6.61; N, 10.83.

Example 50

Z-Leu-Abu-CONH—(CH$_2$)$_3$-1-Tetrahydroquinolinyl.

This compound was synthesized using N-aminopropyltetraquinoline and purified by column chromatography using CHCl$_3$/CH$_3$OH 30:1 (40% yield). Oil, single spot on TLC, $R_f$=0.26 (CHCl$_3$/CH$_3$OH 20:1). $^1$H NMR (CDCl$_3$) ok, MS (FAB) m/e=551 (M+1). Anal: calcd. for C$_{31}$H42N$_4$O$_5$, 550; C, 67.61; H, 7.69; N, 10.17. Found, C, 67.15; H, 7.42; N, 10.02.

Example 51

Z-Leu-Abu-CONH—(CH$_2$)$_3$-2-Tetrahydroisoquinolinyl.

This compound was synthesized using N-aminopropyl-isotetraquinoline and purified by column chromatography using CHCl$_3$/CH$_3$OH 20:1 (20% yield). Yellow semisolid, single spot on TLC, $R_f$=0.51 (CHCl$_3$/CH$_3$OH 20:1 ). $^1$H NMR (CDCl$_3$) ok, MS (FAB) m/e=551 (M+1). Anal: calcd. for C$_{31}$H$_{42}$N$_4$O$_5$, 550; C, 67.61; H, 7.69; N, 10.17. Found, C, 67.23; H, 7.32; N, 9.98.

Example 52

Z-Leu-Abu-CONH—CH$_2$-8-Caffeine.

This compound was synthesized using 8-aminomethylcaffeine and purified by column chromatography using CHCl$_3$/CH$_3$OH 20:1 (30% yield). Yellow solid, single spot on TLC, $R_f$=0.35(CHCl$_3$/CH$_3$OH 10:1), mp 171°–177° C. (dec.). $^1$H NMR (CDCl$_3$) ok, MS (FAB) m/e=556 (16%, M+ 1-28), 471 (100%, M+1-113). Anal: calcd. for C$_{28}$H$_{37}$N$_7$O$_7$, 583; C, 57.62; H, 6.39; N, 16.79. Found, C, 57.70; H, 6.48; N, 16.69.

Example 53

Z-Leu-Abu-CONH—CH$_2$-2-(4-Methyl-2-thiazolyl).

This compound was prepared using synthesized 2-aminomethyl-4-methylthiazole and purified by column chromatography using AcOEt/hexane 6:1 (26% yield). Orange semisolid, single spot on TLC, $R_f$=0.40 (AcOEt/hexane 6:1). $^1$H NMR (CDCl$_3$) ok, MS (FAB, calcd. for C$_{24}$H$_{32}$N$_4$O$_5$S, 488) m/e=489 (3%, M+1), 376 (100%, M+1-113).

Example 54

Z-Leu-Abu-CONH—(CH$_2$)2NH-Biotinyl.

This compound was prepared front Z-Leu-Abu-COOH and biotinylethylenediamine hydrochloride. Biotin (1 g, 4.1 mmole) was dissolved in 20 mL of DMF at 70° C. and cooled to 40° C., CDI (0.97 g, 6 mmole) in 3 mL of DMF was then added when a white precipitate appeared. After stirring at r.t. for two hours, ethylenediamine (1.34 mL, 20 mmole) in 10 mL of DMF was added and stirred for another 3 hours. After evaporating DMF, the semisolid residue was dissolved in 50 mL of refluxing methanol and the unreacted biotin was removed by filtration. The solution was evaporated to dryness, the residue was washed with CHCl$_3$ to remove the imidazole, dissolved in 6 mL of water, acidified to pH 3.0 with 1N HCl, and evaporated to dryness. The crude product was crystallized from methanol to give 1.04 g of biotinylethylenediamine hydrochloride (79% yield). Long spot on TLC, $R_f$=0.21 (butanol:AcOH:H$_2$O=4:1:1), mp 241°–242° C. $^1$H NMR is consistent with the structure.

To a stirred solution of Z-Leu-Abu-COOH (0.6 g, 1.58 mmol) in DMF (15 mL) was added HOBt (0.22 g, 1.58 mmol), DCC (0.49 g, 2.38 mmol), and stirring continued for 2 hours at r.t.(mixture A). To a stirred solution of biotinyl-ethylenediamine hydrochloride (0.6 g, 1.85 mmol) in DMF (10 mL) was added TEA (0.28 mL, 2.03 mmol) at 0°–5° C. and stirred for 2 hours at r.t.(mixture B). To the stirred mixture A was added mixture B and the resulting mixture stirred at room temperature for 3 days and then filtered. The filtrate was evaporated to get a semisolid which was washed with $H_2O$ (30 mL), 1M HCl (30 mL), $H_2O$ (30 mL) and dried under vacuum. Chromatography on a silica gel column using $CHCl_3/CH_3OH$ 5:1 afforded a yellow solid (42% yield). Long spot on TLC, $R_f$=0.41 ($CHCl_3/CH_3OH$ 5:1), mp 188°–192° C (dec.). $^1H$ NMR (DMSO-$d_6$) ok, MS (FAB) m/e=647 (M+1). Anal: calcd. for $C_{31}H_{46}N_6O_7S$, 646; C, 57.56; H, 7.17; N, 12.99. Found, C, 57.04; H, 7.21; N, 13.29.

Example 55

Z-Leu-Abu-CONH—$CH_2$-3-Pyridyl-N-oxide.

This compound was prepared front Z-Leu-Abu-COOH and 3-aminomethylpyridine-N-oxide, and purified by column chromatography using $CHCl_3/CH_3OH$ 20:1 (15% yield). Yellow oil, long spot on TLC, $R_f$=0.40($CHCl_3/CH_3OH_{5:1}$). $^1H$ NMR ($CDCl_3$) ok, MS(FAB, calcd. for $C_{25}H_{32}N_4O_6$, 484) m/e=485 (2%, M+1), 372 (100%, M+1-113).

Example 56

Z-Leu-Abu-CONH—$CH_2$-6-Uracil.

This compound was prepared from Z-Leu-Abu-COOH and 6-aminomethyluracil and purified by column chromatography using $CHCl_3/CH_3OH$ 10:1 (1.5% yield). Brown oil, long spot on TLC, $R_f$=0.28 ($CHCl_3/CH_3OH$ 10:1). $^1H$ NMR ($CDCl_3$) ok, MS (FAB, calcd. for $C_{24}H_{31}N_5O_7$, 501) m/e=389 (100%, M+1-113).

Example 57

Z-Leu-Phe-CONH—$CH_2$-2-Pyridyl.

This compound was prepared from 1,3-dithiolane derivative of Z-Leu-Phe-COOEt and 2-aminomethylpyridine by the procedure described in Example 38, and purified by column chromatography using $CHCl_3/CH_3OH$ 20:1 (41% yield). Yellow solid, long spot on TLC, $R_f$=0.40 ($CHCl_3/CH_3OH$ 20:1 ), mp 144°–146° C. $^1H$ NMR ($CDCl_3$) ok, MS(FAB) m/e=531 (M+1). Anal: calcd. for $C_{30}H_{34}N_4O_5$, 530; C, 67.91; H, 6.46; N, 10.56. Found, C, 67.64; H, 6.50; N, 10.64.

Example 58

Z-Leu-Phe-CONH—$(CH_2)_3$-4-Morpholinyl. This compound was prepared from 1,3-dithiolane derivative of Z-Leu-Phe-COOEt and 4-(3-aminopropyl)morpholine, and purified by column chromatography using $CHCl_3/CH_3OH$ 10: 1(40% yield). Yellow solid, long spot on TLC, $R_f$=0.55 ($CHCl_3/CH_3OH$ 10:1), mp 155°–156° C. $^1H$ NMR ($CDCl_3$) ok, MS (FAB) m/e=581 (M+1). Anal: calcd. for $C_{31}H_{42}N_4O_6$, 566; C, 65.70; H, 7.47; N, 9.89. Found, C, 65.64; H, 7.49; N, 9.84.

Example 59

Z-Leu-Phe-CONH—$CH_2$-2-Quinolinyl.

This compound was prepared using 2-aminomethylquinoline and purified by column chromatography using AcOEt/hexane 1:1 (33% yield). Yellow solid, long spot on TLC, $R_f$=0.30 (AcOEt/hexane 1: 1), mp 131°–135° C. $^1H$ NMR ($CDCl_3$) ok, MS (FAB)m/e=581 (M+1). Anal: calcd. for $C_{34}H_{36}N_4O_5$, 580; C, 70.32; H, 6.25; N, 9.65. Found, C, 70.31; H, 6.27; N, 9.63.

Example 60

Z-Leu-Phe-CONH—$CH_2$-1-Isoquinolinyl.

This compound was prepared using 1-aminomethylisoquinoline and purified by column chromatography using AcOEt/hexane 1:1 (7% yield). Yellow solid, single spot on TLC, $R_f$=0.45 (AcOEt/hexane 1:1),mp 169°–173° C. $^1H$ NMR ($CDCl_3$) ok, MS (FAB) m/e=581 (M+1). Anal: calcd. for $C_{34}H_{36}N_4O_5$, 580; C, 70.32; H, 6.25; N, 9.65. Found, C, 70.05; H, 6.29; N, 9.47.

Example 61

Z-Leu-Phe-CONH—$(CH_2)_3$-1-Tetrahydroquinolinyl.

This compound was prepared using N-aminopropyltetraquinoline and purified by column chromatography using $CHCl_3/CH_3OH$ 30:1 (40% yield). Yellow solid, single spot on TLC, $R_f$=0.58 ($CHCl_3/CH_3OH_{20:1}$),mp 115°–120° C. $^1H$ NMR ($CDCl_3$) ok, MS (FAB) m/e=613 (M+1). Anal: calcd. for $C_{36}H_{44}N_4O_5$, 612; C, 70.56; H, 7.24; N, 9.14. Found, C, 70.46; H, 7.26; N, 9.19.

Example 62

Z-Leu-Phe-CONH—$(CH_2)_3$-2-Tetrahydroisoquinolinyl.

This compound was prepared using N-aminopropylisotetraquinoline and purified by column chromatography using $CHCl_3/CH_3OH$ 20:1 (51% yield). Yellow solid, single spot on TLC, $R_f$=0.62 ($CHCl_3/CH_3OH$ 10:1), mp 107°–111° C. $^1H$ NMR ($CDCl_3$) ok, MS (FAB) m/e=613 (M+1). Anal: calcd. for $C_{36}H_{44}N_4O_5$, 612; C, 70.56; H, 7.24; N, 9.14. Found, C, 69.61; H, 7.25; N, 9.05.

Example 63

Z-Leu-Phe-CONH—$(CH_2)_2$NH-Biotinyl.

This compound was prepared from Z-Leu-Phe-COOH and synthesized biotinylethylenediamine hydrochloride by the procedure described for Example 54, and purified by column chromatography using $CHCl_3/CH_3OH$ 5:1 (35% yield). White solid, long spot on TLC, $R_f$=0.42 ($CHCl_3/CH_3OH$ 5:1), mp 204°–206° C. (dec.). $^1H$ NMR (DMSO-$d_6$) ok, MS (FAB) m/e=709 (M+1). Anal: calcd. for $C_{36}H_{48}N_6O_7S$, 708; C, 60.99; H, 6.82; N, 11.85. Found, C, 61.03; H, 6.83; N, 11.77.

Example 64

Z-Leu-Nva-CONH—$CH_2CH(OH)Ph$.

This compound was synthesized from 1,3-dithiolane derivative of Z-Leu-Nva-COOEt and 2-amino-1-phenylethanol by the procedure described in Example 1, and purified by column chromatography using $CHCl_3/CH_3OH$ 10:1 (54% yield). White solid, single spot on TLC, $R_f$=0.56 ($CHCl_3/CH_3OH$ 10:1), mp 75°–77° C. $^1H$ NMR ($CDCl_3$) ok, MS (FAB, calcd. for $C_{28}H_{37}N_3O_6$, 511) m/e=512(M+1).

Example 65

Z-Leu-Nva-CONH—$CH_2$-2-Pyridyl.

This compound was prepared from 1,3-dithiolane derivative of Z-Leu-Nva-COOEt and 2-aminomethylpyridine by the procedure described in Example 38, and purified by column chromatography using $CHCl_3/CH_3OH$ 10:1 (50% yield). Yellow solid, long spot on TLC, $R_f$=0.55 ($CHCl_3/CH_3OH$ 10:1), mp 65°–70° C. $^1H$ NMR ($CDCl_3$) ok, MS (FAB, calcd. for $C_{26}H_{34}N_4O_5$, 482) m/e=483 (M+1).

Example 66

Z-Leu-Nva-CONH—(CH$_2$)$_3$-4-Morpholinyl.

This compound was prepared from 1,3-dithiolane derivative of Z-Leu-Nva-COOEt and 4-(3-aminopropyl)morpholine, and purified by column chromatography using CHCl$_3$/CH$_3$OH 10:1(37% yield). Yellow solid, long spot on TLC, R$_f$=0.23 (CHCl$_3$/CH$_3$OH 10:1), mp 108°–110° C. $^1$H NMR (CDCl$_3$) ok, MS (FAB, calcd. for C$_{27}$H$_{42}$N$_4$O$_6$, 518) m/e= 519 (M+1).

Example 67

CH$_3$OCO(CH$_2$)$_2$CO-Leu-Abu-CONHEt.

To a solid Z-Leu-Abu-CONHEt (1 g, 2.47 mmol) was added a solution of hydrogen bromide in acetic acid (30 wt %, 1.52 mL, 7.40 mmol) at r.t. The mixture was vigorously stirred for 1 hour during which time all of the ketoamide went into solution. The reaction was quenched with Et$_2$O (30 mL) then separated. The semisolid was triturated and washed successively with Et$_2$O (5×30 mL). After removing solvent, the residue was dried under vacuum, leaving a very hygroscopic solid. $^1$H NMR (CDCl$_3$) showed loss of Z group. The yield was 70–80%.

To a stirred solution of mono-methylsuccinate (0.28 g, 2.13 mmol) in DMF (10 mL) was added DCC (0.44 g, 2.13 mmol) and HOBt (0.29 g, 2.13 mmol). The mixture was stirred for 2 hours at r.t.(mixture A). To a stirred solution of Leu-Abu-CONHEt. HBr (0.5 g, 1.42 mmol) in DMF (5 mL) was added TEA (0.2 mL, 1.42 mmol) at 0°–5° C. and stirred for 30 min (mixture B). To the stirred mixture B was added mixture A at 0°–5° C. and the reaction was stirred overnight at r.t. After evaporation of the solvent, AcOEt (40 mL) was added, the precipitate was filtered, and the filtrate washed with 0.25 N HC$_1$ (10 mL), H$_2$O (20 mL), 10% Na$_2$CO$_3$ (3×20 mL), H$_2$O (20 mL), satd. NaCl (2×20 mL), dried over MgSO$_4$, and concentrated. Chromatography on a silica gel column with CHCl$_3$/CH$_3$OH 10:1 afforded a yellow semisolid (42% yield). Single spot on TLC, R$_f$=0.43 (CHCl$_3$/CH$_3$OH 10:1). $^1$H NMR (CDCl$_3$) ok, MS (FAB, calcd. for C$_{18}$H$_{31}$N$_3$O$_6$, 385) m/e=386 (M+1).

Example 68

2-Furyl-CO-Leu-Abu-CONHEt.

This compound was synthesized using 2-furoic acid by the procedure described for compound 67 and purified by column chromatography using CHCl$_3$/CH$_3$OH 30:1 (39% yield). Yellow solid, single spot on TLC, R$_f$=0.51 (CHCl$_3$/CH$_3$OH10:1), mp 58°–59° C. $^1$H NMR (CDCl$_3$) ok, MS (FAB) m/e=366(M+1). Anal:calcd. for C$_{18}$H$_{27}$N$_3$O$_5$, 365;C, 59.16;H, 7.44; N, 11.50. Found, C, 58.12; H, 7.53; N, 11.64.

Example 69

2-Tetrahydrofuryl-CO-Leu-Abu-CONHEt.

This compound was synthesized using 2-tetrahydrofuroic acid and purified by column chromatography using CHCl$_3$/CH$_3$OH 30:1 (41% yield). Yellow oil, single spot on TLC, R$_f$=0.54 (CHCl$_3$/CH$_3$OH 10:1). $^1$H NMR (CDCl$_3$) ok, MS (FAB, calcd. for C$_{18}$H$_{31}$N$_3$O$_5$, 369) m/e=370 (M+1).

Example 70

3-Pyridyl-CO-Leu-Abu-CONHEt.

This compound was synthesized using nicotinic acid and purified by column chromatography using CHCl$_3$/CH$_3$OH 10:1 (49% yield). Yellow solid, single spot on TLC, R$_f$=0.56 (CHCl$_3$/CH$_3$OH 10:1), mp 57°–61° C. $^1$H NMR (CDCl$_3$) ok, MS (FAB) m/e=377 (M+1). Anal: calcd. for C$_{19}$H$_{28}$N$_4$O$_4$, 376; C, 60.58; H, 7.49; N, 14.92. Found, C, 60.05; H, 7.51; N, 14.58.

Example 71

2-Pyrazinyl-CO-Leu-Abu-CONHEt.

This compound was synthesized using 2-pyrazinecarboxylic acid and purified by column chromatography using CHCl$_3$/CH$_3$OH 10:1 (18% yield). Yellow solid, single spot on TLC, R$_f$=0.33 (CHCl$_3$/CH$_3$OH 10:1), mp 51°–56° C. $^1$H NMR (CDCl$_3$) ok, MS (FAB) m/e=378 (M+1). Anal: calcd. for C$_{18}$H$_{27}$N$_5$O$_4$377; C, 57.29; H, 7.16; N, 18.56. Found, C, 56.74; H, 7.28; N, 18.32.

Example 72

2-Quinolinyl-CO-Leu-Abu-CONHEt.

This compound was synthesized using quinaldic acid and purified by column chromatography using AcOEt/hexane 1:1 (45% yield). Orange solid, single spot on TLC, R$_f$=0.48 (AcOEt/hexane 1:1), mp 56°–59° C. $^1$H NMR (CDCl$_3$) ok, MS (FAB) m/e=427 (M+1). Anal: calcd. for C$_{23}$H$_{30}$N$_4$O$_4$, 426; C, 64.79; H, 7.09; N, 13.13. Found, C, 64.98; H, 7.45; N, 12.48.

Example 73

1-Isoquinolinyl-CO-Leu-Abu-CONHEt.

This compound was synthesized using 1-isoquinoline carboxylic acid and purified by column chromatography using AcOEt/hexane 1:1 (46% yield). Red solid, single spot on TLC, R$_f$=0.47 (AcOEt/hexane 1:1),mp 104°–106° C. $^1$H NMR (CDCl$_3$) ok, MS (FAB) m/e=427 (M+1). Anal: calcd. for C$_{23}$H$_{30}$N$_4$O$_4$, 426; C, 64.79; H, 7.09; N, 13.13. Found, C, 65.00; H, 7.31; N, 12.96.

Example 74

4-Morpholinyl-CO-Leu-Abu-CONHEt.

This compound was synthesized from 4-morpholinecarbonyl chloride (1 mmol), Leu-AbuCONH-Et.HBr (1 mmol) and TEA (2.5 mmol), and purified by column chromatography using CHCl$_3$/CH$_3$OH 10:1 (33% yield). Yellow oil, single spot on TLC, R$_f$=0.45 (CHCl$_3$/CH$_3$OH 10:1). $^1$H NMR (CDCl$_3$) ok, MS (FAB, calcd. for C18H$_{32}$N$_4$O$_5$, 384) m/e=385 (M+1).

Example 75

Ph(CH$_2$)$_2$CO-Leu-Abu-CONHEt.

This compound was synthesized from 1,3-dithiolane derivative of Ph(CH$_2$)$_2$CO-Leu-Abu-COOEt and EtNH$_2$, and purified by column chromatography using CHCl$_3$/CH$_3$OH 30:1 (72% yield). Yellow solid, single spot on TLC, R$_f$=0.23(CHCl$_3$/CH$_3$OH 30:1),mp 134°–136° C. $^1$H NMR (CDCl$_3$) ok, MS (FAB) m/e=404 (M+1). Anal: calcd. for C$_{22}$H$_{33}$N$_3$O$_4$403; C, 65.48; H, 8.24; N, 9.60. Found, C, 65.52; H, 8.30; N, 9.42.

Example 76

1-C$_{10}$H$_7$CH$_2$CO-Leu-Abu-CONHEt.

This compound was synthesized from 1,3-dithiolane derivative of 1-C$_{10}$H$_7$CO-Leu-Abu-COOEt and EtNH$_2$, and purified by column chromatography using CHCl$_3$/CH$_3$OH 30:1 (67% yield). Yellow solid, single spot on TLC, R$_f$=0.47 (CHCl$_3$/CH$_3$OH 30: 1), mp 201°–203° C. $^1$H NMR (CDCl$_3$) ok, MS (FAB) m/e=440 (M+1). Anal: calcd. for $C_{25}H_{33}N_3O_4$, 439; C, 68.31; H, 7.57; N, 9.56. Found, C, 68.19; H, 7.52; N, 9.49.

Example 77

Ph$_2$CHCO-Leu-Abu-CONHEt.

This compound was synthesized from 1,3-dithiolane derivative of Ph$_2$CHCO-Leu-Abu-COOEt and EtNH$_2$, and purified by column chromatography using CHCl$_3$/CH$_3$OH 10:1 (24% yield). Yellow solid, single spot on TLC, $R_f$=0.40 (CHCl$_3$/CH$_3$OH 10: 1), mp 78°–83° C. $^1$H NMR (CDCl$_3$) ok, MS (FAB) m/e=467 (M+1). Anal: calcd. for $C_{27}H_{35}N_3O_4$, 466; C, 69.65; H, 7.58; N, 9.02. Found, C, 70.04; H, 7.72; N, 8.72.

Example 78

Ph$_2$CHCO-Leu-Abu-CONH—CH$_2$CH(OH)Ph.

This compound was synthesized from 1,3-dithiolane derivative of Ph$_2$CHCO-Leu-Abu-COOEt and 2-amino-1-phenylethanol, and purified by column chromatography using CHCl$_3$ followed by CHCl$_3$/CH$_3$OH 30:1 (30% yield.). Yellow solid, single spot on TLC, $R_f$=0.40 (AcOEt/hexane 1:1), mp 178°–180° C. $^1$H NMR (CDCl$_3$) ok, MS (FAB) m/e=558 (M+1). Anal: calcd. for $C_{33}H_{39}N_3O_5$, 557; C, 71.07; H, 7.05; N, 7.53. Found, C, 70.93; H, 7.10; N, 7.46.

Example 79

Ph$_2$CHCO-Leu-Abu-CONH-2-CH$_2$-Pyridyl.

This compound was prepared from 1,3-dithiolane derivative of Ph$_2$CHCO-Leu-Abu-COOEt and 2-aminomethylpyridine, and purified by column chromatography using CHCl$_3$ following by CHCl$_3$/AcOEt 7:3 (9% yield), mp 161–163. Yellow solid, single spot on TLC, $R_f$=0.30 (CHCl$_3$/CH$_3$OH 10:1). $^1$H NMR (CDCl$_3$) ok, MS (FAB) m/e=529 (M+1). Anal: calcd. for $C_{31}H_{36}N_4O_4$, 528; C, 70.43; H, 6.86; N, 10.60. Found, C, 70.42; H, 6.91; N, 10.47.

Example 80

Ph$_2$CHCO-Leu-Abu-CONH—N—(CH$_2$)$_3$-Morpholinyl.

This compound was prepared from 1,3-dithiolane derivative of Ph$_2$CHCO-Leu-Abu-COOEt and N-aminopropylmorpholine, and purified by column chromatography using CHCl$_3$ followed by CHCl$_3$/AcOEt 7:3 (25% yield), mp 170–174. Yellow solid, single spot on TLC, $R_f$=0.25 (CHCl$_3$/CH$_3$OH 10:1). $^1$H NMR (CDCl$_3$) ok, MS (FAB) m/e=565 (M+1). Anal: calcd. for $C_{32}H_{44}N_4O_5$, 564; C, 68.06; H, 7.85; N, 9.92. Found, C, 67.22; H, 7.77; N, 9.75.

Example 81

Ph$_2$CHCO-Leu-Phe-CONH—CH$_2$CH(OH)Ph.

This compound was prepared from 1,3-dithiolane derivative of Ph$_2$CHCO-Leu-Phe-COOEt and 2-amino-1-phenylethanol, and purified by crystallization from CHCl$_3$/ether (16% yield). Yellow solid, single spot on TLC, $R_f$=0.41 (AcOET/CH$_3$OH 9: 1), mp 192°–196° C. $^1$H NMR (CDCl$_3$) ok, MS (FAB) m/e=620 (M+1). Anal: calcd. for $C_{38}H_{41}N_3O_5$, 619; C, 73.64; H, 6.67; N, 6.78. Found, C, 72.00; H, 6.62; N, 6.41.

Example 82

Ph$_2$CHCO-Leu-Phe-CONH—CH$_2$-2-Pyridyl.

This compound was synthesized from 1,3-dithiolane derivative of Ph$_2$CHCO-Leu-Phe-COOEt and 2-aminomethylpyridine, and purified by column chromatography using CHCl$_3$ following by CHCl$_3$/AcOEt 9:1 (9% yield). Yellow solid, single spot on TLC, $R_f$=0.33 (AcOET/CH$_3$OH 9:1), mp 160°–162° C. $^1$H NMR (CDCl$_3$) ok, MS (FAB) m/e=591 (M+1). Anal: calcd. for $C_{36}H_{38}N_4O_4$, 590; C, 73.20; H, 6.48; N, 9.48. Found, C, 69.91; H, 6.29; N, 8.98.

Example 83

Ph$_2$CHCO-Leu-Phe-CONH—(CH$_2$)$_3$-4-Morpholinyl.

This compound was synthesized from 1,3-dithiolane derivative of Ph$_2$CHCO-Leu-Phe-COOEt and N-aminopropylmorpholine, and purified by column chromatography using AcOEt followed by crystallization from AcOEt/ether (20% yield). Yellow solid, single spot on TLC, Rf =0.45 (AcOET/CH$_3$OH 9:1), mp 158°–160° C. $^1$H NMR (CDCl$_3$) ok, MS (FAB) m/e=627 (M+1). Anal: calcd. for $C_{37}H_{46}N_4O_5$, 626; C, 70.90; H, 7.40; N, 8.94. Found, C, 70.05; H, 7.43; N, 8.68.

It is obvious that those skilled in the art may make modifications to the invention without departing from the spirit of the invention or the scope of the subjoined claims and their equivalents.

What is claimed is:

1. A compound of the formula:

or a pharmaceutically acceptable salt, wherein

Y is selected from the group consisting of $C_{1-4}$ alkyl monosubstituted with phenyl, $C_{1-4}$ alkyl disubstituted with phenyl, $C_{1-4}$ alkyl monosubstituted with 1-naphthyl, $C_{1-4}$ alkyl monosubstituted with 2-naphthyl, $C_{1-4}$ alkoxy monosubstituted with phenyl, $C_{1-4}$ alkoxy disubstituted with phenyl, ArCH$_2$O—, ArO—, ArCH$_2$NH—, ArNH—, $M^1$—(CH$_2$)$_q$—, and $M^2$—(CH$_2$)$_q$—O—;

wherein Ar is selected from the group consisting of phenyl, phenyl monosubstituted with J, phenyl disubstituted with J, 1-naphthyl, 1-naphthyl monosubstituted with J, 2-naphthyl, and 2-naphthyl monosubstituted with J;

J is selected from the group consisting of halogen, OH, CN, NO$_2$, NH$_2$, COOH, CO$_2$Me, CO$_2$Et, CF$_3$, $C_{1-4}$ alkoxy, $C_{1-4}$ alkylamine, $C_{2-8}$ dialkylamine, $C_{1-4}$ perfluoroalkyl, and —N(CH$_2$CH$_2$)$_2$O;

$M^1$ is selected from the group consisting of 2-furyl, 2-tetrahydrofuryl, 2-pyridyl, 3-pyridyl, 4-pyridyl, 2-pyrazinyl, 2-quinolinyl, 1-tetrahydroquinolinyl, 1-isoquinolinyl, 2-tetrahydroisoquinolinyl, and —N(CH$_2$CH$_2$)$_2$O;

q=0–2;

$M^2$ is selected from the group consisting of 2-furyl, 2-tetrahydrofuryl, 2-pyridyl, 2-pyrazinyl, 2-quinolinyl, 2-tetrahydroquinolinyl, 1-isoquinolinyl, and 1-tetrahydroisoquinolinyl;

AA$^2$ is an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-cyclohexyl)-COOH, NH$_2$—CH(CH$_2$-cyclopentyl)-COOH, NH$_2$—CH(CH$_2$-cyclobutyl)—COOH, NH$_2$—CH(CH$_2$-cyclopropyl)COOH, 5,5,5-trifluoroleucine, and hexafluoroleucine;

AA¹ is an amino acid with the L configuration, D configuration, or DL configuration at the α-carbon selected from the group consisting of alanine, 4-chlorophenylalanine, valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, NH₂—CH(CH₂CHEt₂)-COOH, alpha-aminoheptanoic acid, NH₂—CH(CH₂-1-napthyl)-COOH, NH₂—CH(CH₂-2-napthyl)-COOH, NH₂—CH(CH₂-cyclohexyl)-COOH, NH₂— CH(CH₂-cyclopentyl)-COOH, NH₂—CH(CH₂-cyclobutyl)-COOH, NH₂—CH(CH₂-cyclopropyl)-COOH, 5,5,5-trifluoroleucine, and hexafluoroleucine;

X is selected from the group consisting of
a) —CH₂CH(OH)—R¹ and
b) —(CH₂)$_n$—R³;

R¹ is selected from the group consisting of phenyl, phenyl monosubstituted with J, phenyl disubstituted with J, phenyl trisubstituted with J, pentafluorophenyl,

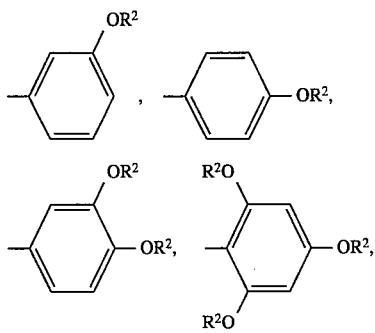

1-naphthyl, 1-naphthyl monosubstituted with J, 1-naphthyl disubstituted with J, 2-naphthyl, 2-naphthyl monosubstituted with J, 2-naphthyl disubstituted with J, 2-pyridyl, 2-quinolinyl, and 1-isoquinolinyl;

R² represents C$_{1-4}$ alkyl, C$_{1-4}$ alkyl substituted with phenyl, phenyl, and phenyl substituted with J;
n=1–3;
R³ is selected from the group consisting of 2-furyl, 2-furyl monosubstituted with J, 2-pyridyl, 2-pyridyl monosubstituted with J, 3-pyridyl, 3-pyridyl monosubstituted with J, 4-pyridyl, 4-pyridyl monosubstituted with J, 2-quinolinyl, 2-quinolinyl monosubstituted with J, 1-isoquinolinyl, 1-isoquinolinyl monosubstituted with J,

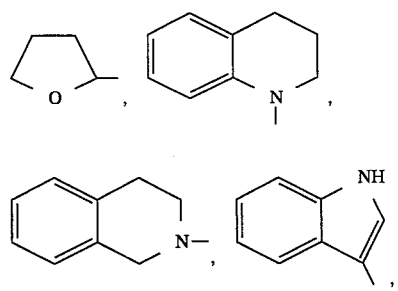

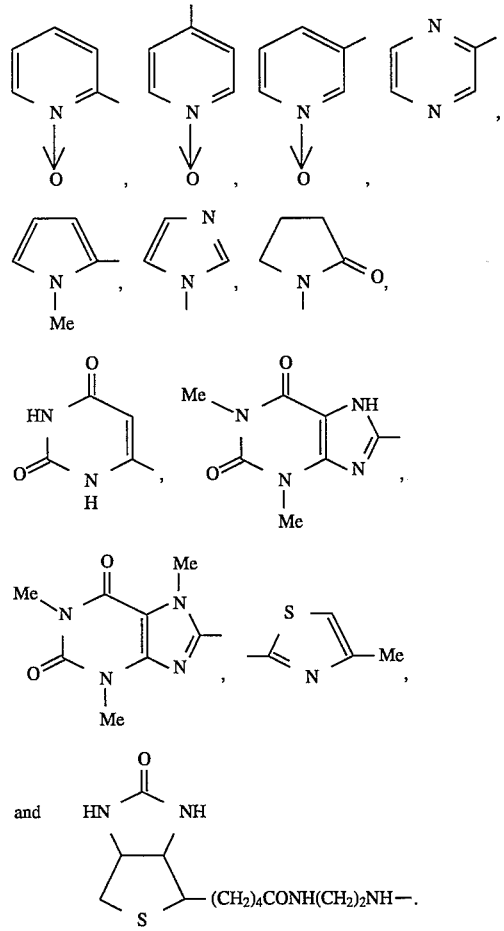

and HN—C(=O)—NH— (CH₂)₄CONH(CH₂)₂NH—.

2. A compound of the formula:

Y—CO—AA²—AA¹—CO—NH—X or a pharmaceutically acceptable salt as claimed in claim 1, wherein Y is selected from the group consisting of C$_{1-4}$ alkyl monosubstituted with phenyl, C$_{1-4}$ alkyl disubstituted with phenyl, C$_{1-4}$ alkyl monosubstituted with 1-naphthyl, C$_{1-4}$ alkyl monosubstituted with 2-naphthyl, C$_{1-4}$ alkoxy monosubstituted with phenyl, C$_{1-4}$ alkoxy disubstituted with phenyl, ArCH₂O—, ArO—, ArCH₂NH—, and ArNH—;

X is —CH₂CH(OH)—R¹.

3. A compound of the formula:

Y—CO—AA²—AA¹—CO—NH—X or a pharmaceutically acceptable salt as claimed in claim 2, wherein Y is selected from the group consisting of PhCH₂CH₂—, Ph₂CH—, 1-naphthyl-CH₂—, 2-naphthyl-CH₂—, PhCH₂O—, Ph₂CHO—, 1-naphthyl-CH₂O—, 2-naphthyl-CH₂O—, PhCH₂NH—, 1-naphthyl-CH₂NH—, and 2-naphthyl-CH₂NH—;

AA² is selected from the group consisting of leucine, isoleucine, valine, and methionine;

AA¹ is selected from the group consisting of phenylalanine, alpha-aminobutyric acid, norleucine, norvaline, methionine, and 4-chlorophenylalanine;

5,514,694

51

R¹ is selected from the group consisting of phenyl, 1-naphthyl, 2-naphthyl,

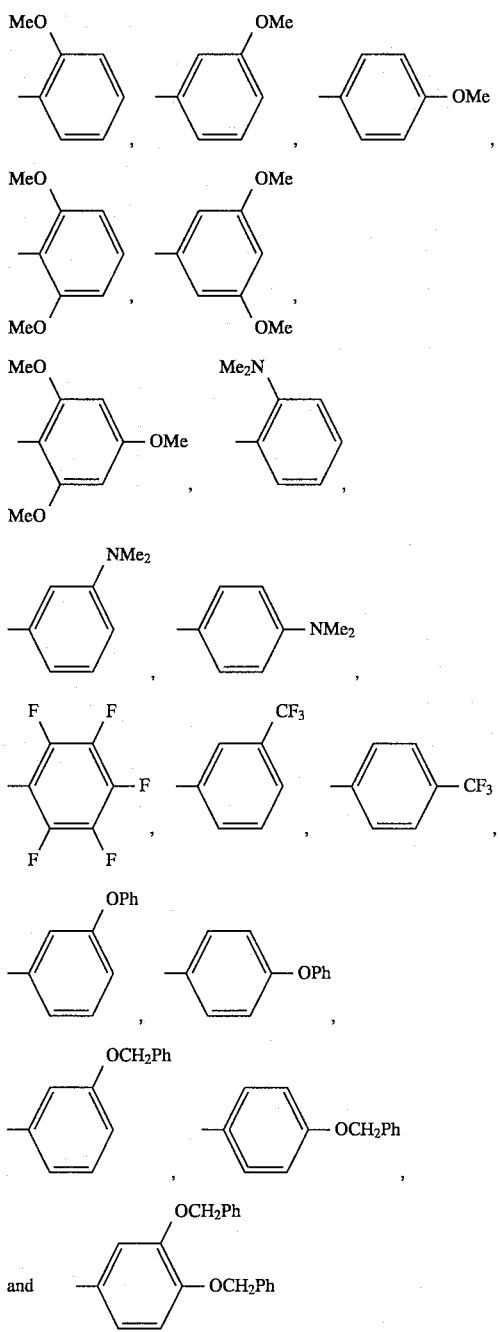

and

4. A compound of the formula:

Y—CO—AA²—AA¹—CO—NH—X or a pharmaceutically acceptable salt as claimed in claim 1, wherein Y is selected from the group consisting of $C_{1-4}$ alkyl monosubstituted with phenyl, $C_{1-4}$ alkyl disubstituted with phenyl, $C_{1-4}$ alkyl monosubstituted with 1-naphthyl, $C_{1-4}$ alkyl monosubstituted with 2-naphthyl, $C_{1-4}$ alkoxy monosubstituted with phenyl, $C_{1-4}$ alkoxy disubstituted with phenyl, ArCH₂O—, ArO—, ArCH₂NH—, and ArNH—; X is —(CH₂)$_n$—R³.

5. A compound of the formula:

52

Y—CO—AA²—AA¹—CO—NH—X or a pharmaceutically acceptable salt as claimed in claim 4, wherein Y is selected from the group consisting of PhCH₂CH₂—, Ph₂CH—, 1-naphthyl-CH₂—, 2-naphthyl-CH₂—, PhCH₂O—, Ph₂CHO—, 1-naphthyl-CH₂O—, 2-naphthyl-CH₂O—, PhCH₂NH—, 1-naphthyl-CH₂NH—, and 2-naphthyl-CH₂NH—;

AA² is selected from the group consisting of leucine, isoleucine, valine, and methionine;

AA¹ is selected from the group consisting of phenylalanine, alpha-aminobutyric acid, norleucine, norvaline, methionine, and 4-chlorophenylalanine;

R³ is selected from the group consisting of 2-furyl, 2-pyridyl, 3-pyridyl, 4-pyridyl, 2-quinolinyl, 1-isoquinolinyl,

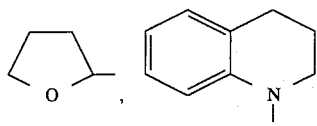

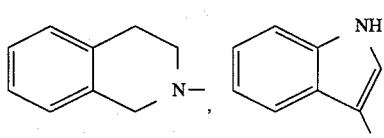

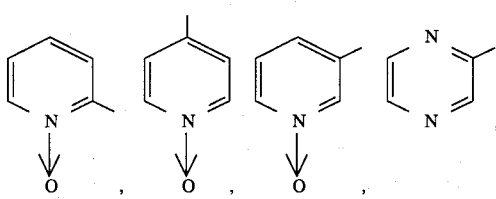

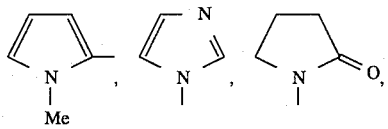

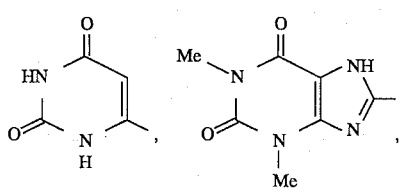

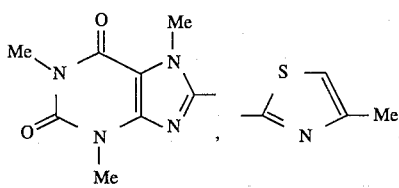

and 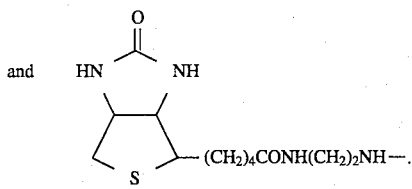 —(CH₂)₄CONH(CH₂)₂NH—.

6. A compound of the formula:

or a pharmaceutically acceptable salt as claimed in claim 1, wherein

Y is $M^1-(CH_2)_q-$;

X is $-CH_2CH(OH)-R^1$.

7. A compound of the formula:

or a pharmaceutically acceptable salt as claimed in claim 6, wherein

AA² is selected from the group consisting of leucine, isoleucine, valine, and methionine;

AA¹ is selected from the group consisting of phenylalanine, alpha-aminobutyric acid, norleucine, norvaline, methionine, and 4-chlorophenylalanine;

R¹ is selected from the group consisting of phenyl, 1-naphthyl, 2-naphthyl,

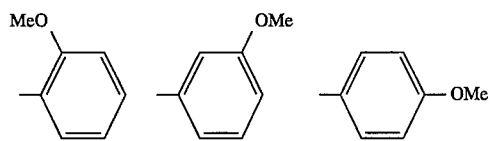

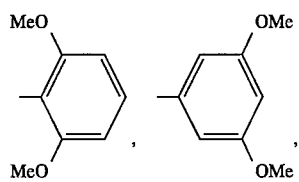

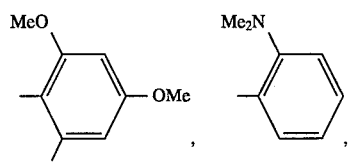

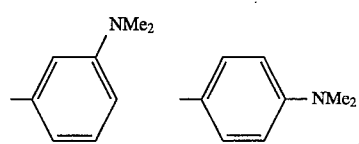

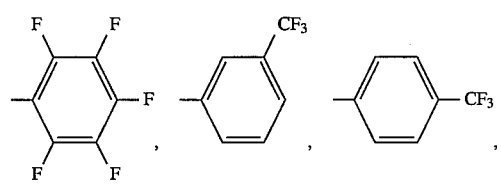

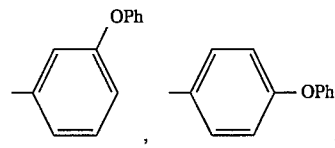

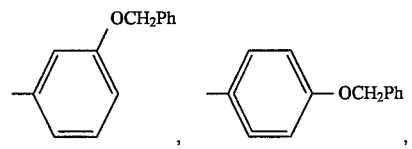

-continued

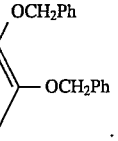

and

8. A compound of the formula:

or a pharmaceutically acceptable salt as claimed in claim 1, wherein

Y is $M^1-(CH_2)_q-$;

X is $-(CH_2)_n-R^3$.

9. A compound of the formula:

or a pharmaceutically acceptable salt as claimed in claim 8, wherein

AA² is selected from the group consisting of leucine, isoleucine, valine, and methionine;

AA¹ is selected from the group consisting of phenylalanine, alpha-aminobutyric acid, norleucine, norvaline, methionine, and 4-chlorophenylalanine;

R³ is selected from the group consisting of 2-furyl, 2-pyridyl, 3-pyridyl, 4-pyridyl, 2-quinolinyl, 1-isoquinolinyl,

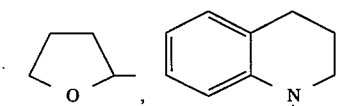

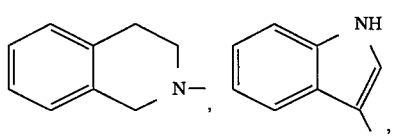

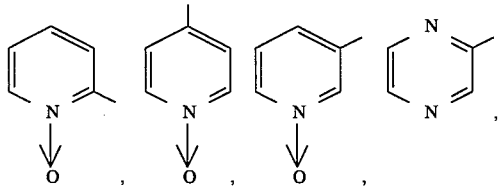

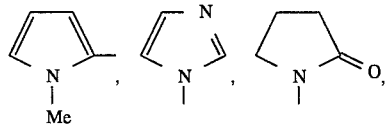

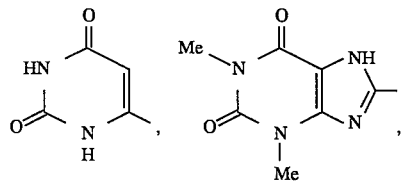

55

-continued

[structure: dimethylxanthine-imidazole carboxamide], [thiazole with Me], and [bicyclic thiolactam with (CH₂)₄CONH(CH₂)₂NH—].

10. A compound of the formula:

Y—CO—AA²—AA¹—CO—NH—X or a pharmaceutically acceptable salt as claimed in claim 1, wherein Y is M²—(CH₂)$_q$—O—;
X is —CH₂CH(OH)—R¹.

11. A compound of the formula:

Y—CO—AA²—AA¹—CO—NH—X or a pharmaceutically acceptable salt as claimed in claim 10, wherein AA² is selected from the group consisting of leucine, isoleucine, valine, and methionine;

AA¹ is selected from the group consisting of phenylalanine, alpha-aminobutyric acid, norleucine, norvaline, methionine, and 4-chlorophenylalanine;

R¹ is selected from the group consisting of phenyl, 1-naphthyl, 2-naphthyl,

[various methoxy- and dimethylamino-substituted phenyl structures: 2-MeO-phenyl, 3-MeO-phenyl, 4-MeO-phenyl, 2,3-(MeO)₂-phenyl, 2,5-(MeO)₂-phenyl, 3,4,5-(MeO)₃-phenyl, 2-Me₂N-phenyl, 3-Me₂N-phenyl, 4-Me₂N-phenyl],

56

-continued

[pentafluorophenyl, 3-CF₃-phenyl, 4-CF₃-phenyl, 3-OPh-phenyl, 4-OPh-phenyl, 3-OCH₂Ph-phenyl, 4-OCH₂Ph-phenyl], and [2,3-bis(OCH₂Ph)-phenyl].

12. A compound of the formula:

Y—CO—AA²—AA¹—CO—NH—X or a pharmaceutically acceptable salt as claimed in claim 1, wherein Y is M²—(CH₂)$_q$—O—;
X is —(CH₂)$_n$—R³.

13. A compound of the formula:

Y—CO—AA²—AA¹—CO—NH—X or a pharmaceutically acceptable salt as claimed in claim 12, wherein AA² is selected from the group consisting of leucine, isoleucine, valine, and methionine;

AA¹ is selected from the group consisting of phenylalanine, alpha-aminobutyric acid, norleucine, norvaline, methionine, and 4-chlorophenylalanine;

R³ is selected from the group consisting of 2-furyl, 2-pyridyl, 3-pyridyl, 4-pyridyl, 2-quinolinyl, 1-isoquinolinyl,

[tetrahydrofuran-2-yl, 1,2,3,4-tetrahydroquinolinyl, 1,2,3,4-tetrahydroisoquinolinyl, indolyl/indoline structures],

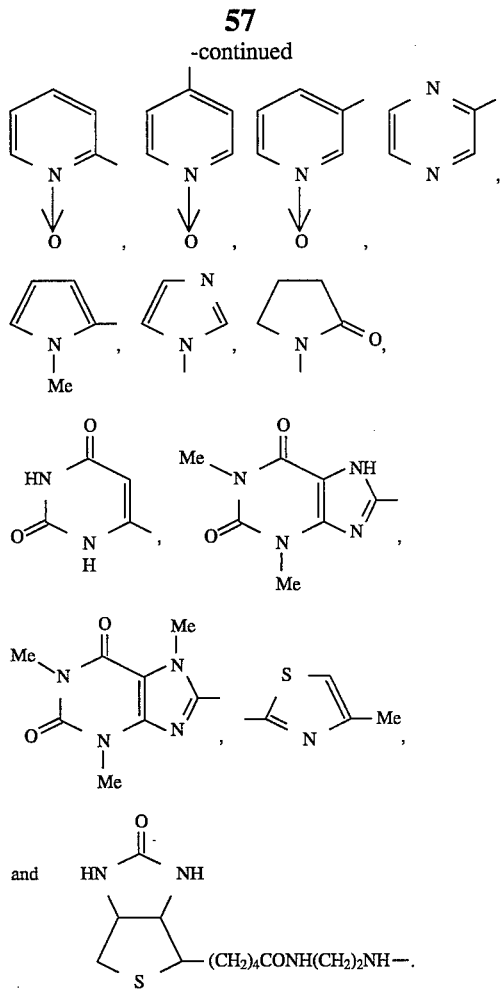

14. A compound selected from the group consisting of:
(a) Z-Leu-Abu-CONH—(CH$_2$)$_2$OH,
(b) Z-Leu-Abu-CONH—(CH$_2$)$_5$OH,
(c) Z-Leu-Abu-CONH—(CH$_2$)$_2$O(CH$_2$)$_2$OH,
(d) Z-Leu-Abu-CONH—CH$_2$CH(OCH$_3$)$_2$,
(e) Z-Leu-Abu-CONH—CH$_2$CH(OC$_2$H$_5$)$_2$,
(f) Z-Leu-Abu-CONH—CH$_2$—C$_6$H$_8$[1,3,3-(CH$_3$)$_3$-5-OH],
(g) Z-Leu-Abu-CONH—(CH$_2$)$_2$C$_6$H$_4$(4-OH),
(h) Z-Leu-Abu-CONH—(CH$_2$)$_2$C$_6$H$_4$(2-OCH$_3$),
(i) Z-Leu-Abu-CONH—(CH$_2$)$_2$C$_6$H$_4$(3-OCH$_3$),
(j) Z-Leu-Abu-CONH—(CH$_2$)$_2$C$_6$H$_4$(4-OCH$_3$),
(k) Z-Leu-Abu-CONH—CH$_2$C$_6$H$_3$[3,5-(OCH$_3$)$_2$],
(l) Z-Leu-Abu-CONH—CH$_2$CH(OH)Ph,
(m) Z-Leu-Abu-CONH—CH$_2$CH(OH)C$_6$H$_4$(4-OCH$_3$),
(n) Z-Leu-Abu-CONH—CH$_2$CH(OH)C$_6$H$_2$[2,4,6-(OCH$_3$)$_3$],
(o) Z-Leu-Abu-CONH—CH$_2$CH(OH)C$_6$H$_4$[4-N(CH$_3$)$_2$],
(p) Z-Leu-Abu-CONH—CH$_2$CH(OH)C$_6$F$_5$,
(q) Z-Leu-Abu-CONH—CH$_2$CH(OH)C$_6$H$_4$(3-CF$_3$),
(r) Z-Leu-Abu-CONH—CH$_2$CH(OH)C$_6$H$_4$(3-OPh),
(s) Z-Leu-Abu-CONH—CH$_2$CH(OH)C$_6$H$_4$(4-OPh),
(t) Z-Leu-Abu-CONH—CH$_2$CH(OH)C$_6$H$_4$(4-OCH$_2$Ph),
(u) Z-Leu-Abu-CONH—CH$_2$CH(OH)C$_6$H$_4$-3-OC$_6$H$_4$(3-CF$_3$),
(v) Z-Leu-Abu-CONH—CH$_2$CH(OH)C$_6$H$_4$-3-OC$_6$H$_3$(3,4-Cl$_2$),
(w) Z-Leu-Abu-CONH—CH$_2$CH(OH)C$_6$H$_3$[3,4-(OCH$_2$Ph)$_2$],
(x) Z-Leu-Abu-CONH—CH$_2$CH(OH)-1-C$_{10}$H$_7$,
(y) Z-Leu-Abu-CONH—CH$_2$CH(OH)-2-C$_{10}$H$_7$,
(z) Z-Leu-Phe-CONH—CH$_2$CH(OH)Ph,
(aa) Z-Leu-Phe-CONH—CH$_2$CH(OH)C$_6$H$_4$[4-N(CH$_3$)$_2$],
(bb) Z-Leu-Phe-CONH—CH$_2$CH(OH)C$_6$F$_5$,
(cc) Z-Leu-Phe-CONH—CH$_2$CH(OH)C$_6$H$_4$(3-CF$_3$),
(dd) Z-Leu-Phe-CONH—CH$_2$CH(OH)C$_6$H$_4$(3-OPh),
(ee) Z-Leu-Phe-CONH—CH$_2$CH(OH)C$_6$H$_4$(4-OPh),
(ff) Z-Leu-Phe-CONH—CH$_2$CH(OH)C$_6$H$_4$(4-OCH$_2$Ph),
(gg) Z-Leu-Phe-CONH—CH$_2$CH(OH)C$_6$H$_4$-3-OC$_6$H$_4$(3-CF$_3$),
(hh) Z-Leu-Phe-CONH—CH$_2$CH(OH)C$_6$H$_4$-3-OC$_6$H$_3$(3,4-Cl$_2$),
(ii) Z-Leu-Phe-CONH—CH$_2$CH(OH)C$_6$H$_3$(3,4-(OCH$_2$Ph)$_2$),
(jj) Z-Leu-Abu-CONH—CH$_2$-2-furyl,
(kk) Z-Leu-Abu-CONH—CH$_2$-2-tetrahydrofuryl,
(ll) Z-Leu-Abu-CONH—CH$_2$-2-pyridyl,
(mm) Z-Leu-Abu-CONH—CH$_2$-3-pyridyl,
(nn) Z-Leu-Abu-CONH—CH$_2$-4-pyridyl,
(oo) Z-Leu-Abu-CONH—(CH$_2$)$_2$-2-pyridyl,
(pp) Z-Leu-Abu-CONH—CH$_2$-2-pyridyl(3—COOCH$_3$),
(qq) Z-Leu-Abu-CONH—CH$_2$-2-pyridyl(5—COOCH$_3$),
(rr) Z-Leu-Abu-CONH—(CH$_2$)$_2$-2-(N-methylpyrrolyl),
(ss) Z-Leu-Abu-CONH—(CH$_2$)$_3$-1-imidazolyl,
(tt) Z-Leu-Abu-CONH—(CH$_2$)$_2$-4-morpholinyl,
(uu) Z-Leu-Abu-CONH—(CH$_2$)$_3$-4-morpholinyl,
(vv) Z-Leu-Abu-CONH—(CH$_2$)$_3$-1-pyrrolidinyl-2-one,
(ww) Z-Leu-Abu-CONH—(CH$_2$)$_2$-3-indolyl,
(xx) Z-Leu-Abu-CONH—CH$_2$-2-quinolinyl,
(yy) Z-Leu-Abu-CONH—CH$_2$-1-isoquinoline,
(zz) Z-Leu-Abu-CONH—(CH$_2$)$_3$-1-tetrahydroquinolinyl,
(aaa) Z-Leu-Abu-CONH—(CH$_2$)$_3$-2-tetrahydroisoquinolinyl,
(bbb) Z-Leu-Abu-CONH—CH$_2$-8-caffeinyl,
(ccc) Z-Leu-Abu-CONH—CH$_2$-2-(4-methyl-2-thiazolyl),
(ddd) Z-Leu-Abu-CONH-CONH—(CH$_2$)$_2$NH-biotinyl,
(eee) Z-Leu-Abu-CONH—CH$_2$-3-pyridyl-N-oxide,
(fff) Z-Leu-Abu-CONH—CH$_2$-6-uracil,
(ggg) Z-Leu-Phe-CONH—CH$_2$-2-pyridyl,
(hhh) Z-Leu-Phe-CONH—(CH$_2$)$_3$-4-morpholinyl,
(iii) Z-Leu-Phe-CONH—CH$_2$-2-quinolinyl,
(jjj) Z-Leu-Phe-CONH—CH$_2$-1-isoquinolinyl,
(kkk) Z-Leu-Phe-CONH—(CH$_2$)$_3$-1-tetrahydroquinolinyl,
(lll) Z-Leu-Phe-CONH—(CH$_2$)$_3$-2-tetrahydroisoquinolinyl,
(mmm) Z-Leu-Phe-CONH—(CH$_2$)$_2$-NH-biotinyl,
(nnn) Z-Leu-Nva-CONH—CH$_2$CH(OH)Ph,
(ooo) Z-Leu-Nva-CONH—CH$_2$-2-pyridyl,
(ppp) Z-Leu-Nva-CONH—(CH$_2$)$_3$-4-morpholinyl,
(qqq) CH$_3$OCO(CH$_2$)$_2$CO-Leu-Abu-CONHEt,
(rrr) 2-furyl-CO-Leu-Abu-CONHEt,
(sss) 2-tetrahydrofuryl-CO-Leu-Abu-CONHEt,
(ttt) 3-pyridyl-CO-Leu-Abu-CONHEt,
(uuu) 2-pyrazyl-CO-Leu-Abu-CONHEt,
(vvv) 2-quinolinyl-CO-Leu-Abu-CONHEt,
(www) 1-isoquinolinyl-CO-Leu-Abu-CONHEt,
(xxx) 4-morpholinyl-CO-Leu-Abu-CONHEt,
(yyy) Ph(CH$_2$)$_2$CO-Leu-Abu-CONHEt,
(zzz) 1-C$_{10}$H$_7$CH$_2$CO-Leu-Abu-CONHEt,
(aaaa) Ph$_2$CHCO-Leu-Abu-CONHEt,
(bbbb) Ph$_2$CHCO-Leu-Abu-CONH—CH$_2$CH(OH)Ph,
(cccc) Ph$_2$CHCO-Leu-Abu-CONH—CH$_2$-2-pyridyl,
(dddd) Ph$_2$CHCO-Leu-Abu-CONH—(CH$_2$)$_3$-4-morpholinyl,
(eeee) Ph$_2$CHCO-Leu-Phe-CONH—CH$_2$CH(OH)Ph,
(ffff) Ph$_2$CHCO-Leu-Phe-CONH—CH$_2$-2-pyridyl, and
(gggg) Ph$_2$CHCO-Leu-Phe-CONH—(CH$_2$)$_3$-4-morpholinyl.

* * * * *